(12) United States Patent
Schlicker et al.

(10) Patent No.: US 7,385,392 B2
(45) Date of Patent: Jun. 10, 2008

(54) EDDY CURRENT SENSING ARRAYS AND SYSTEM

(75) Inventors: Darrell E. Schlicker, Watertown, MA (US); Neil J. Goldfine, Newton, MA (US); Eric L. Miller, Waban, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 691 days.

(21) Appl. No.: 10/155,887

(22) Filed: May 23, 2002

(65) Prior Publication Data

US 2002/0163333 A1 Nov. 7, 2002

Related U.S. Application Data

(63) Continuation-in-part of application No. 10/010,062, filed on Nov. 13, 2001, now abandoned.

(60) Provisional application No. 60/248,104, filed on Nov. 13, 2000.

(51) Int. Cl.
  *G01N 27/82* (2006.01)
  *G01R 33/12* (2006.01)

(52) U.S. Cl. ........ 324/242; 324/260

(58) Field of Classification Search ........ 324/238–240, 324/242, 659, 681, 686, 690, 260, 262; 702/38, 702/115, 124
  See application file for complete search history.

(56) References Cited

U.S. PATENT DOCUMENTS

| | | | |
|---|---|---|---|
| 3,611,126 A * | 10/1971 | Lucka | 324/662 |
| 4,271,393 A | 6/1981 | Hansen et al. | |
| 4,303,885 A | 12/1981 | Davis et al. | |
| 4,423,371 A | 12/1983 | Senturia et al. | |
| 4,912,414 A | 3/1990 | Lesky et al. | |
| 4,928,246 A * | 5/1990 | Crawley et al. | 700/8 |
| 5,015,951 A | 5/1991 | Melcher | |
| 5,047,719 A | 9/1991 | Johnson et al. | |
| 5,182,513 A | 1/1993 | Young et al. | |
| 5,262,722 A | 11/1993 | Hedengren et al. | |
| 5,371,461 A | 12/1994 | Hedengren | |
| 5,371,462 A | 12/1994 | Hedengren et al. | |
| 5,389,876 A | 2/1995 | Hedengren et al. | |
| 5,399,968 A * | 3/1995 | Sheppard et al. | 324/242 |
| 5,629,621 A | 5/1997 | Goldfine et al. | |
| 5,793,206 A | 8/1998 | Goldfine et al. | |
| 5,966,011 A | 10/1999 | Goldfine et al. | |
| 6,037,768 A * | 3/2000 | Moulder et al. | 324/225 |
| RE36,986 E | 12/2000 | Melcher | |
| 6,188,218 B1 | 2/2001 | Goldfine et al. | |
| 6,198,279 B1 | 3/2001 | Goldfine | |
| 6,601,009 B2 * | 7/2003 | Florschuetz | 702/124 |
| 7,107,337 B2 * | 9/2006 | Barrow et al. | 709/224 |

* cited by examiner

*Primary Examiner*—Reena Aurora
(74) *Attorney, Agent, or Firm*—Hamilton, Brook, Smith & Reynolds, P.C.

(57) ABSTRACT

An apparatus that measures electrical impedance. The apparatus includes a signal generator controlled by a master microcontroller, a plurality of data acquisition channels, each channel containing a microcontroller, a host computer that processes and stores measured values, and a communication line between the host computer and the master microcontroller.

32 Claims, 14 Drawing Sheets

EDDY CURRENT SENSING ARRAYS AND SYSTEM

RELATED APPLICATIONS

This application is a continuation-in part of U.S. application Ser. No. 10/010,062, filed Nov. 13, 2001 now abandoned, which claims the benefit of U.S. Provisional Application No. 60/248,104, filed Nov. 13, 2000.

The entire teachings of the above applications are incorporated herein by reference.

BACKGROUND

Nondestructive measurements of materials can be performed with a variety of sensors operating on different physical principles, such as electromagnetic, acoustic, or thermal sensors, where the properties of the material influence the response of the sensor. Electrical measurements at the sensor terminal, such as the electrical impedance or admittance, are then used to determine the material properties. These material properties may reflect characteristics of the bulk material condition such as heat treatment, state of cure, fatigue damage, or porosity, surface conditions such as roughness, shot peen intensity, coating thickness, and coating condition, or the presence of defects such as cracks, inclusions, or service-related aging.

In many inspection applications, large surface areas of a material need to be tested. This inspection can be accomplished with a single sensor and a two-dimensional scanner over the material surface. However, use of a single sensor has disadvantages in that the scanning can take an excessively long time and care must be taken when registering the measured values together to form a map or image of the properties. These shortcomings can be overcome by using an array of sensors or an array of elements within a single sensor, as described for example in U.S. Pat. No. 5,793,206, since the material can be scanned in a shorter period of time and the measured responses from each array element are spatially correlated. However, the use of arrays complicates the instrumentation used to determine the response of each array element. For example, in one conventional method, as described for example in U.S. Pat. No. 5,182,513, the response from each element of an array is processed sequentially by using a multiplexer for each element of the array. While this is generally faster than scanning a single sensor element, there is still a significant time delay as the electrical signal settles for each element and there is the potential for signal contamination from previously measured channels. An alternative is to use a separate impedance instrument for each array element. However, this can significantly add to the cost of the system, since the impedance instrumentation tends to be expensive compared to the sensors or array elements.

For nondestructive testing of conducting and/or magnetic materials over wide areas, eddy current sensor arrays may be used. These eddy current sensors excite a conducting winding, the primary, with an electrical current source of a prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. When scanning over wide areas, these arrays may include several individual sensors, but each sensor must be driven sequentially in order to prevent cross-talk or cross-contamination between the sensing elements. Another approach is to use a single drive winding and an array of sense elements, described for example in U.S. Pat. No. 5,793,206.

There is also a need for methods that make calibration and measurement procedures self-consistent so that the resulting measurements are robust and reproducible to justify implementation in production or field inspection applications. Conventional eddy current "pencil probes" used for inspection of engine components, for example, are often calibrated using crack standards. For example, the signal from a typical crack might be recorded and then the range on the instrument might be set so that the crack response is at 80% of the total scale. Then, a threshold might be set so that some minimum crack size is detectable on the standard. This is a useful method if the crack standard well represents the actual component that is being inspected for cracks. Unfortunately, standards that are flat and contain simulated flaws (e.g., fatigue cracks grown from EDM notches with the notches later broached and then the surface etched to "reveal" the cracks) are generally used to determine the POD (probability of detection) for a given flaw size. This is a useful method only when the component is well represented by the standard. If, for example, the probe scanning the actual component is at a higher lift-off (e.g., proximity of the sensor to the surface is not as close) than it was on the standard when the thresholds were set, then the actual detectable crack size would be larger (and perhaps much larger) than assumed.

SUMMARY

This invention relates to instrumentation and apparatus for the nondestructive measurements of materials. In one embodiment, the instrumentation architecture has multiple microcontroller-based measurement channels that perform the data acquisition. Each measurement channel has the same basic structure so that more channels can be added by plugging in new boards, without changing the architecture so that the instrument is scalable. A master microcontroller provides general control to the instrument while the microcontroller for each measurement channel controls data acquisition for each channel. The measurements are then stored, processed, and displayed on a central processor such as a host computer. In another embodiment, the host computer is connected to the master microcontroller with a serial line for data communication and each channel microcontroller passes data to the host computer through the master microcontroller. In another embodiment, separate data communication lines are used for each microcontroller on the instrument. The master microcontroller and the channel microcontrollers may also share the same communication lines. In another embodiment, the data channel measures the terminal impedance in parallel, at basically the same time, as any other data acquisition channels. In another embodiment, the instrument is connected to at least one probe element for measurements. These measurements may be performed with test circuits of eddy current sensing elements or capacitive sensing elements.

In another embodiment, eddy current sensing element array test circuit designs are disclosed that permit the creation of images when scanned over a material surface. In one form, a linear array of sensing elements is placed between a pair of linear drive winding segments. In another form, a second linear array of elements is placed parallel to the first array. This second array can also be offset in a direction parallel to the linear array by a portion of the dimension of a sensing element to facilitate complete coverage of the test material when the sensing array is scanned. In a preferred embodiment, all of the sensing elements have the same sensing area dimensions and the offset distance is one-half the length of the sensing element. Individual connections to each sensing element make rapid imaging possible. In another embodiment, the second linear array of elements is placed next to the first array within the same pair of drive winding segments, with both sets of sensing elements having the same distance to the nearest drive winding. With the sensing elements aligned in the scan direction, perpendicular to the array direction, the differential response between aligned sensing elements can be performed. Alternatively, the second array can be offset in a direction parallel to the linear array by a portion of the dimension of a sensing element. In another embodiment, two arrays are located on opposite sides of a linear drive. The elements of each array are aligned, with no offset, the signals from elements on opposite sides are both recorded, and filters are used to improve sensitivity to flaws using both element responses. In one embodiment, the signal from sensing elements on opposite sides are compared so that the response to small anomalies should be the same as sensing elements on opposite sides of the drive. In another embodiment, multiple frequencies are used to improve sensitivity.

In another embodiment, eddy current sensing element array test circuit designs are disclosed that provide sensitivity to multiple penetration depths into the test material. This is accomplished by placing the sensing elements at different distances to the linear drive winding segments. In one embodiment, all of the sensing elements are placed between a single pair of drive segments. In another embodiment, at least one sensing element is placed between a different pair of drive segments. A portion of the sensing elements can also comprise two linear arrays of elements that are placed on either side of a single large element at the center between the drive segments. Differential measurements can be performed with the linear arrays of elements and absolute measurements can be performed.

In another embodiment, methods are disclosed for processing the measurements to extract desired information. In one embodiment, images or one dimensional scans of the measured properties are filtered by matching the measured response to a characteristic shape for a defect, or anomaly. In another embodiment, the thresholds for detection are set by determining the signal-to-noise ratio based on the background material properties and the response to anomalies of interest. In another embodiment, varying the orientation of the sensor relative to the orientation of the defect can increase or decrease the sensitivity to the defect.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
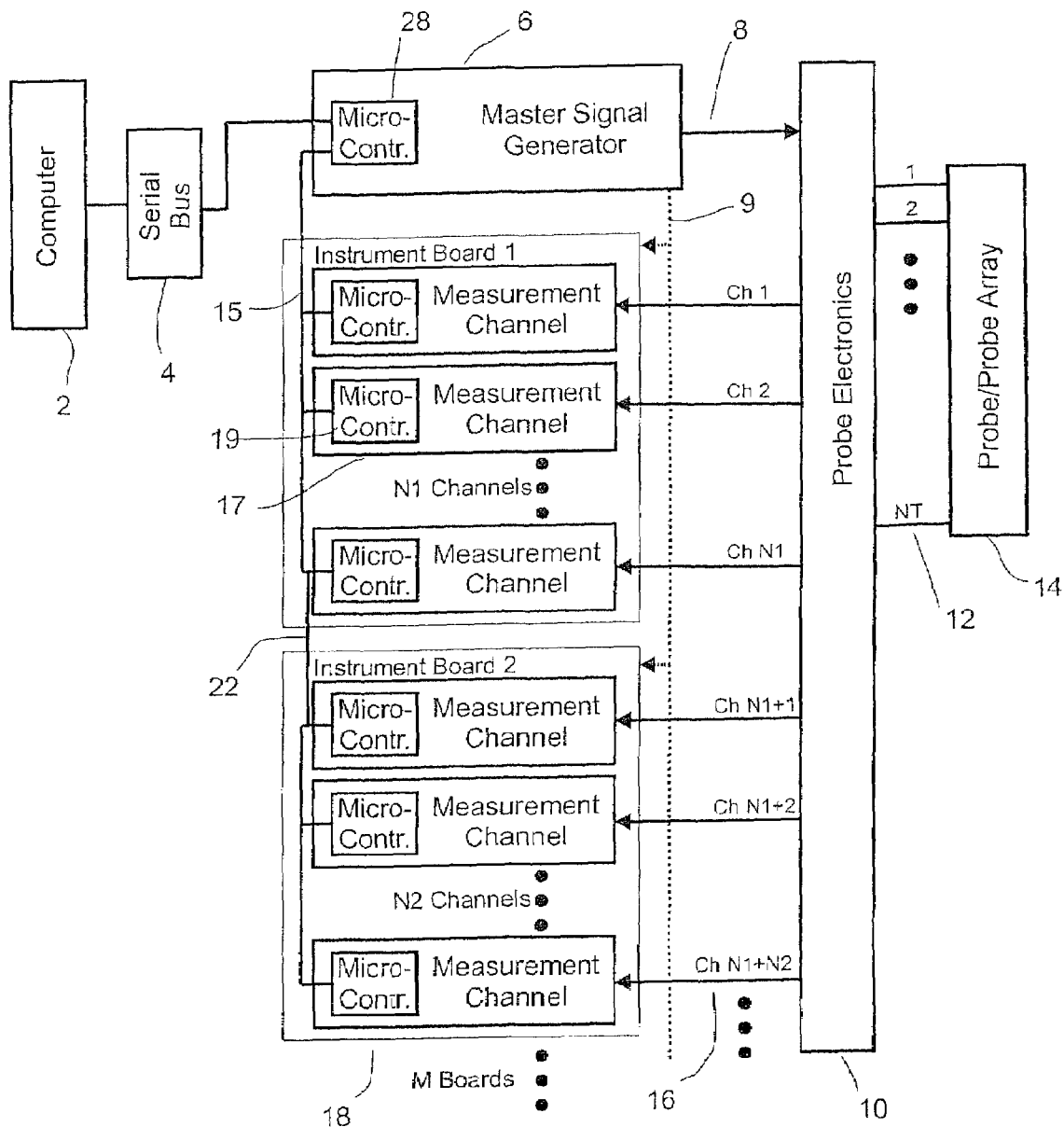
FIG. 1 is a simplified schematic for a multiple channel, parallel data acquisition impedance instrument architecture.

In FIG. 1 a schematic for a multi-channel impedance measurement apparatus is shown which has microcontroller based signal generation and data acquisition components along with remote (probe) electronics for connection to a sensor array. The apparatus contains a computer 2 for setting parameters for the measurements, such as the excitation frequency, and for providing the capability to process, display, and store measured values. The computer 2 communicates with microcontrollers 28 on the master signal generator 6 through a digital serial bus 4, such as an RS422. Alternatively, the bus 4 can be a parallel bus which connects the computer 2 to the microcontroller 28. The master microcontroller then communicates and controls the microcontrollers 19 on the instrument or data acquisition boards 18 through a digital line 15. On line 15, handshaking and control signals are sent to the microcontrollers 17 on the instrument boards while measurement data is sent back up to the master microcontroller 28. Additional boards are connected together in a series fashion to the digital line 15 through a jumper connection 22. The microtrollers 17 coordinate with each other to handle the data logistics. Additionally or alternatively, the microcontroller 28 handles the data logistics. The signal generator 6 creates a sinusoidal drive signal 8, at a frequency specified by the computer 2, which is passed into the probe electronics 10. The drive signal can be amplified in the probe electronics 10 or converted into the appropriate form (voltage or current source) for excitation for the probe or probe array 14. For example, for eddy current or inductive sensors, where the current through a drive coil or winding creates the magnetic field for the measurement, the excitation is typically an electrical current. For dielectric or capacitive sensors, where the voltage on drive electrodes creates the electric field for the measurement, the excitation is typically an electrical voltage. The electrical signals 12 from each individual probe element then passes through the probe electronics 10, for amplification, buffering, and/or filtering. The result is a separate signal or channel 16 for each probe element which are converted into digital signals by the measurement channels 17 on the data acquisition boards 18. A drive information line 9, which can contain a reference signal and even drive signal information, is passed to the data acquisition boards 18. Processing of each signal as part of the data acquisition includes filtering the signal, comparing the signal to a reference signal to determine components that are in phase and in quadrature, converting from analog to digital forms, storing the signal, and passing the measurement data back to the computer 2.

The architecture of FIG. 1 shows an embodiment for connecting M instrument boards together and numerous measurement channels. Each instrument board has drive signal information lines 9 and communication lines 15 (via 22) connections. The number of channels on each instrument board can vary, indicated as N1 on instrument board one, N2 on instrument board two, and so on. It is generally desirable to have each of the instrument boards have the same number of channels so that repairs and replacements can more easily be performed. Also, if the probe array has NT elements being used in a measurement, it desirable to have at least NT+1 measurement channels. The extra measurement channel is used to measure the drive signal. Additional extra channels can be included for multiple drives.

In one embodiment, the microcontroller 28 controls each of the microcontrollers on the instrument boards 19 through the signals on line 15. In another embodiment, which further promotes the scalability of the architecture, the master microcontroller 28 only directly controls the first microcontroller 17 on each instrument board. The first microcontroller on each board then controls the communication between each of the microcontrollers on an instrument board and the host computer. This first microcontroller determines the number of serial ports being used and determines if the board works with its own serial port or if the serial port from a previous board is to be used. In another embodiment, portions of this instrumentation might be combined into an ASIC format. Also, in place of the computer 2, the microcontroller 28 can operate as a master or host processor or computer which controls the operation of the multi-channel impedance measurement apparatus. The microcontroller 28 can also serve as the local microcontrollers for the measurement channels, and/or can provide data storage.

There are several advantages of this design for the instrumentation architecture. One is the scalability or flexibility to include numerous data acquisition boards without requiring redesign of the instrumentation. For measurements with a single channel or small numbers of array elements, less than approximately eight, a single instrument board can be used. For measurements with larger arrays, greater than eight, additional boards can be stacked onto the first board. A second advantage is the distribution of the microcontrollers between the various signal generation and data acquisition boards. Distributing the microcontrollers allows one to take advantage of relatively fast digital communications between microcontrollers. This is analogous to a distributed computer network where numerous computers or microprocessors can be linked. The use of digital serial bus 4 also allows the distance between the central processing unit (2) and the measurement instrumentation (6 and 18) to be relatively long, up to hundreds of feet. A third advantage is the use of a separate measurement channel for each element of the probe array. This greatly improves the rate with which data can be acquired as multiplexing between the elements is not required. Conventional instrumentation multiplexes between the probe elements, which is a relatively slow process. Multiplexing also raises the issue of signal contamination from previously measured channels.

Another advantage for this instrumentation architecture is that modest control is passed to the local microcontrollers for each measurement channel. When power is first applied, the master microcontroller sends signals to each of the measurement channel microcontrollers giving them a unique channel number and providing the number of measurements and frequencies that will be required. Each measurement channel microcontroller performs zeroing operations to remove nominal offsets and then performs the required number of measurements. Each measurement channel microcontroller is then triggered sequentially for transmission of data back to the host computer and sends a handshake signal back to the master microcontroller when the operation is complete. The microcontroller in the first position on each of the instrument boards provides further control for board level functions. This microcontroller determines if the board needs to respond to the master microcontroller signals and in essence provides a modular plug and play capability.

Utilizing distributed processing for each or for a subset of measurement channels optimizes physical distances for high bandwidth data paths while scaling processing power to maintain a true parallel architecture especially with increasing channel counts.

Although the configuration in FIG. 1 provides a simple, single connection between the computer and the instrument via the master microcontroller, the data is transmitted twice: from the instrument board microcontrollers to the master microcontroller and then from the master microcontroller to the host computer. To increase the throughput, a configuration similar to FIG. 2 can be used, where the data transmission lines 26 are separated from the control lines to the master microcontroller 28. When possible, the same numbers as used in FIG. 1 are also used in FIG. 2. In this configuration, the master microcontroller 28 provides control and handshake signals with the microcontrollers for each measurement channel via a signal line 23. This line is jumpered 22 between boards to provide a common control line so that each measurement channel microcontroller is triggered at the appropriate time to transmit the data to the computer. The data is transmitted along a common data bus 24 on each instrument board and connected to the common signal line 26 for each of the instrument boards. To further improve thoughput and performance, more than one serial port can be used on the computer. The number of instrument boards connected to each serial line and serial port is arbitrary. In a preferred embodiment, the first data acquisition board shares the same serial port as the master microcontroller while the second data acquisition board uses a second serial port.

Figure 2:
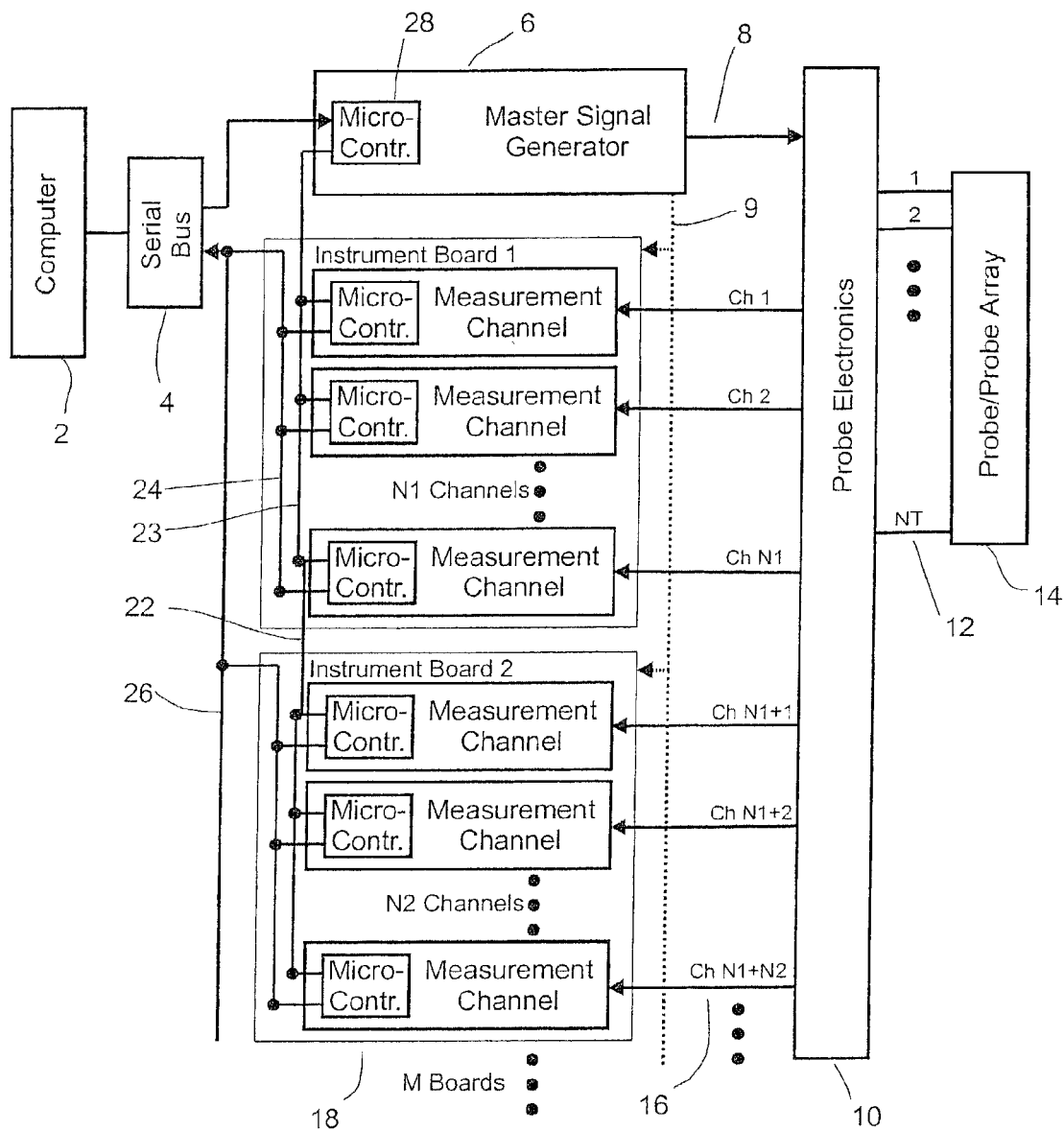
FIG. 2 is a schematic for a multiple channel, parallel data acquisition impedance instrument architecture with separate data transmission and channel control lines.
Figure 3:
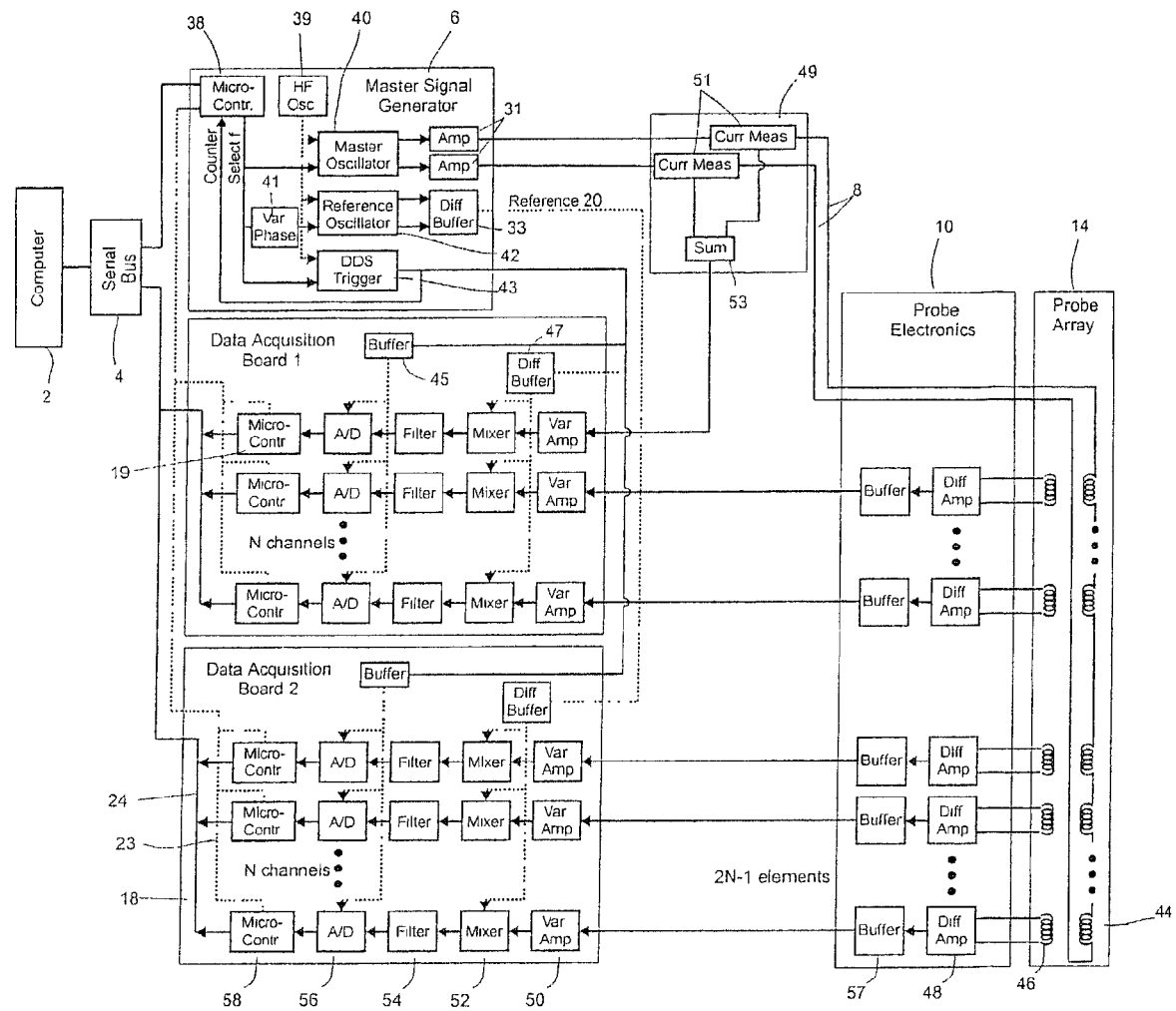
FIG. 3 is a schematic for a multiple channel, parallel data acquisition eddy current sensor instrument.

In FIG. 3 a detailed embodiment for a scalable impedance measurement instrument is shown with application to an eddy current probe sensing array. When possible, the same numbers as used in FIG. 1 and FIG. 2 are also used here. The host computer 2 communicates with the master microcontroller 38 for control of the instrument and receives measurement data from the data acquisition boards 18 through a serial bus 4. Software in the computer takes the raw measurement signals from the instrument and converts these signals into desired values, such as impedances, admittances, and voltage or current gains. The final conversion of the data is performed in the computer to provide a reconfigurable measurement system.

The microcontroller 38 controls the generation of the drive signal, sending a common frequency select signal to a master oscillator 40, a reference oscillator 42, and a trigger 43. The frequency select signal steps-down the signal from a common high frequency oscillator 39. For measurements from 1 Hz to 30 MHz, a high frequency oscillator signal of 120 MHz is adequate. The output of the oscillators is a differential sinusoid signal because more drive current can be obtained with lower voltage levels and it helps to reduce common mode (capacitive) coupling of noise signals to the sensing elements. For the master or drive signal, both components of the signal are amplified with a variable gain amplifier 31 and passed through a circuit 49 for measuring the signal level. This is accomplished through current measuring circuits 51 that are then summed 53, with the resultant signal sent through one of the measurement channels. This direct measurement of the drive signal 8 helps improve the quality of the impedance measurement as drive signal levels vary, particularly over broad frequency ranges. For the reference signal, the signal from the microcontroller passes through a variable phase element 41, which shifts the reference signal phase relative to the drive. This allows measurement of both the in-phase and quadrature phase signals with a single measurement channel, as described below. The differential output of the reference oscillator 42 is then buffered 33 and passed 20 to each data acquisition board. The trigger is used to enable the analog-to-digital conversions on each measurement channel and is passed down to each data acquisition board. The trigger signal is also passed back to the master microcontroller 38 and counted so that the master microcontroller can keep track of the number of measurements that have been performed. Both of the oscillators and the trigger are direct digital synthesizers (DDS's) which allow all of the generated signals to be synchronized and phase-locked with respect to each other.

The drive signal 8 is passed through the probe electronics 10 before entering the probe array 14. The probe array in these cases consists of a series of primary or drive inductive windings or coils 44 with sensing secondary windings or coils 48 distributed within the footprint of the primary windings. An example sensing array would be a Meandering Winding Magnetometer (MWM™), which has a spatially periodic primary winding pattern with secondary windings distributed throughout the primary winding meanders or an array of MWMs. The voltage induced on each secondary winding 48 is then amplified and buffered 57 to drive the signal lines to the data acquisition boards 18. This voltage can be measured as the differential voltage across each secondary element or, if one side of the secondary elements is grounded, as a single sided measurement. The induced voltage depends upon the properties of and proximity to the MUT. The signals from the secondary elements are then amplified with a variable gain amplifier 50 at the input to the data acquisition board 18 prior to processing. The variable gain setting can be controlled individually or set at the same time by either the master microcontroller 38 or the microcontroller 19 for each channel. Processing could include mixing 52 with the reference signal 20 to determine the components of the signal in phase and in quadrature. This can be accomplished with a four quadrant multiplier circuit. In the presently preferred embodiment in-phase detection is employed, quadrature component detection being achieved by shifting the reference signal to be in quadrature with the drive signal. Alternatives considered include multiple driving frequencies and/or use of both in-phase and quadrature detection simultaneously by dedicating two channels to each signal. The signal is also filtered 54, with analog active filters or passive filters (such as a fifth order elliptical active filter using a voltage controlled voltage source topology) to remove high frequency signal variations. This signal is then sampled and held for conversion from analog to digital form and being buffered in the A/D converters 56. Internal buffers in the A/D converters 56 provide storage for the signals prior to being accessed by the microcontrollers 58 for transmission back to the computer 2.

The drive signal is also passed back through to the data acquisition board 18. This allows for a precise measurement of the drive signal, along with the signals induced on the secondary elements 48. Comparing each secondary signal to the drive signal then provides an accurate method for determining the impedance between each secondary element and the drive. As a result, for a given board with N channels or M boards of N channels each, one channel is reserved for the drive signal and the remaining channels can be allocated for the measurement of signals from each secondary element. In FIG. 3, two N channel boards are illustrated so that 2N–1 channels are available for measurements of signals from the probe array. In a preferred embodiment, the drive current measurement circuitry 49 is moved into the probe electronics 10. This is particularly valuable for relatively high frequency measurements where capacitive effects can alter the signal level 8 before it reaches the probe electronics 10 or probe array 14. In another embodiment, multiple drive channels are included.

Each data acquisition board 18 has several common elements, in addition to the modular measurement channels. A buffer 45 is used for maintaining the trigger signal magnitude. A buffer for the differential reference signal 47 maintains the reference signal magnitude. The communication line 23 allows the master microcontroller 38 to communicate and trigger each channel microcontroller 19. In addition, each channel microcontroller can send handshaking signals back to the master microcontroller to keep each microcontroller synchronized. The transmission line 24 sends data form each microcontroller back through the serial bus 4 to the host computer 2.

A typical measurement cycle starts with the master microcontroller setting the frequency and creating drive and reference signals. The variable phase for the reference signal is initially set to zero degrees. After waiting for the output of the filter 54 to settle, a measurement is taken of the DC component of the filtered signal. The channel microcontroller then receives the data from the analog-to-digital converter, averages it and signals the master microcontroller that it is ready for the next measurements. This is repeated until a preset number of measurements (set by the host computer) have been performed. The reference signal phase is then shifted by 90 degrees and the measurement procedure repeated to get the quadrature phase information. For data transmission, the master microcontroller signals each board or bank of measurement channels to begin transmitting data simultaneously and the data is transmitted from each channel on a board sequentially.

An enabling feature of this instrumentation architecture is that the components such as the analog-to-digital converters and the microcontrollers can now be made into a small and compact size. This allows the instrumentation data acquisition boards to be fabricated into a reasonable size and at a reasonable expense. Furthermore, the phase of the reference oscillator can be set in real-time for measuring the in-phase and quadrature-phase signal levels. Thus, no transients in the drive and sense lines of the probe electronics and probe array will be created as the reference phase is shifted. Furthermore, both components of the signal are measured with the same circuit components, eliminating the effects of any slight variations between measurement channels when two different circuits are used to determine the in-phase and quadrature phase signal components. In one embodiment, the footprint of the instrumentation can be further reduced using either ASICs or chip sets.

When operating at frequencies below the cutoff frequency for the filter 54, which is typically 20 kHz, other measurement procedures can be performed to provide high quality signal measurements. For frequencies slightly below cutoff frequency, the reference and measured signals can be synchronized so that measurements can be performed over an integer number of excitation signal cycles. For very low frequencies, measurements can be performed at reasonable fixed intervals throughout the signal period. Multiplication of the signal levels with function tables for determining the in-phase and quadrature phase components can then be performed in software, rather than hardware, when there is sufficient time between measurements. Averaging of the signal can also be performed while the multiplication is being performed. The oscillator frequency can also be set to zero frequency and the phase adjusted so that the DC signal level from the filter falls within a nominal magnitude for the analog-to-digital conversion boards.

In alternative embodiments, the drive signal 8 can be further amplified in the probe electronics module 10, prior to being sent into the probe array 14. The buffers 57 in the probe electronics 10 can also be converted into variable gain amplifiers for additional control over the signal levels from the various array elements.

In one embodiment, the master microcontroller 28 configures the frequency and output level of a drive current, which is applied to a drive winding of array 14. Voltages induced on sensing elements 46 are buffered and amplified by probe electronics 10 and provided to instrument channel 6 as signal 16. At excitation frequencies greater than twice the cut-off frequency of low-pass filter 54 the signal is mixed (multiplied) by a reference signal 20. This reference signal 20 is configured with a frequency matching the excitation signal and a phase, which can be changed by 90 degrees. The mixed signal is then filtered by low-pass filter 54 leaving a DC components which is related to the in-phase or quadrature component of signal 16 depending on the configuration of reference 20. A/D converter 56 then converts the analog signal to digital signal, which is read by channel microcontroller 58. Channel microcontroller 58 provides noise filtering on data from A/D converter 56, which results in a reduction in the quantity of data, for example, through averaging or a more complex filter. Channel microcontroller 58 provides the capability to read data from its A/D converter 56 and provides filtering in parallel simultaneously with other measurement channels. The reduction in data during the filtering operation reduces the bandwidth requirement of data paths routing the data back to a central location, such as host computer 2. At excitation frequencies below cut-off frequency of filter 54, the reference 20 is set with a DC signal and additional correlation techniques provided by microcontroller 58 recover in-phase and quadrature components of signal 16. The master microcontroller 28 coordinates A/D converter measurements, data transmission and frequency selection.

Figure 4:
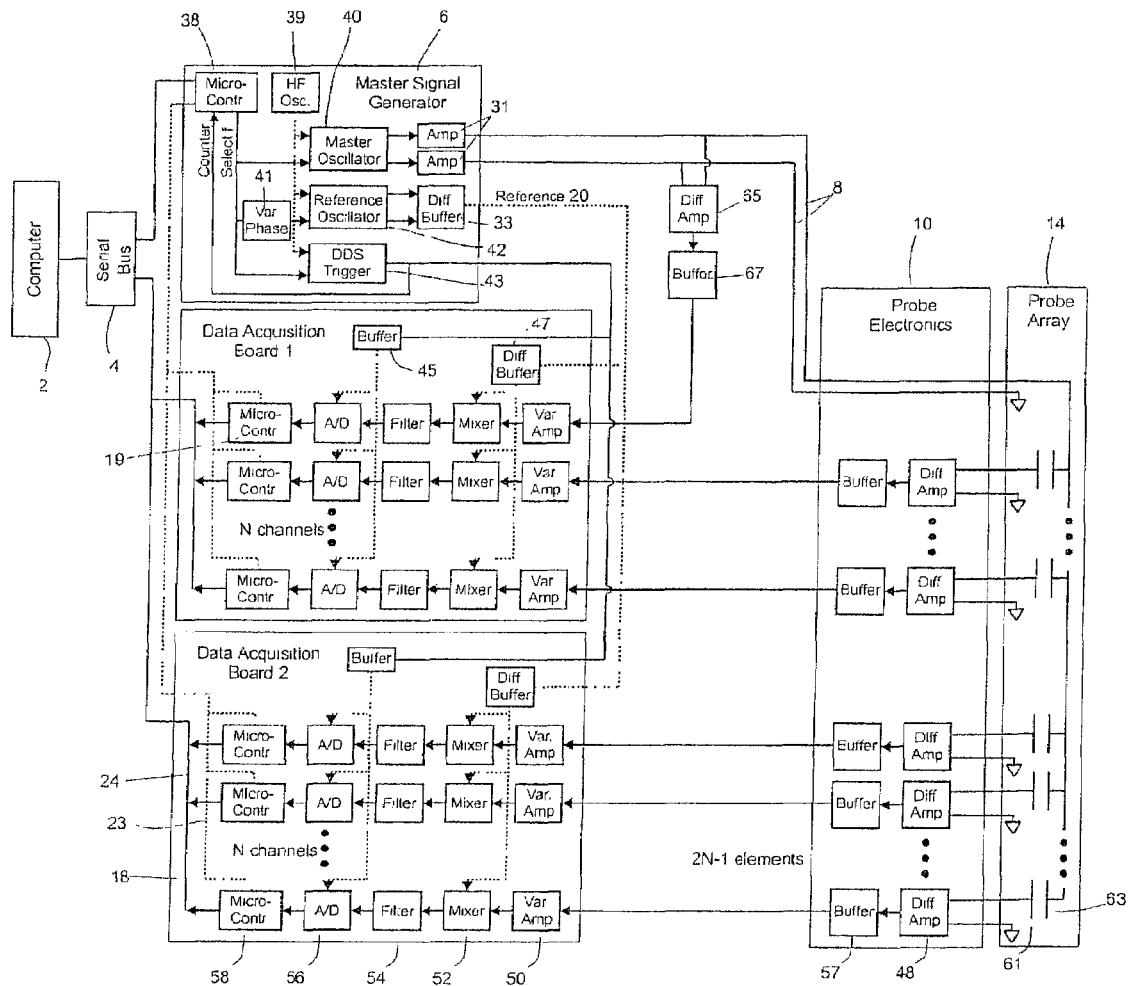
FIG. 4 is a schematic for a multiple channel, parallel data acquisition capacitive sensor instrument.

FIG. 4 shows an instrument configuration for a capacitive sensing array. It is essentially the same as FIG. 3 for the eddy current sensing array except for the drive signal and the probe array. In this case, the drive signal 8 is assumed to be a sinusoidal voltage which is measured by a differential amplifier 65, buffered 67 and passed through to a measurement channel on a data acquisition board. The drive signal may be amplified in the probe electronics, if necessary, and is connected to one or more drive elements 63 that couple to sense elements 61 capacitively through an electric field. The generation of the signals, measurements on the various channels, and communication with the host computer are as described previously.

This distributed processing and buffering for the individual data channels allows for greatly increased data acquisition rates over multiplexed measurement systems. Separation of the signal sampling operation from the signal transmission allows measurement data to be obtained while the earlier (buffered) signals are being transmitted back to the computer 2. Furthermore, the individual buffers for each channel, as opposed to a single buffer or storage element for all channel, allows large numbers of channels to be added to the instruments without compromising the data acquisition rate. As long as the measurement time is greater than the transmission time for the data, the measurement time is the limiting factor. This is especially useful when trying to obtain real-time high resolution images of material properties; for imaging applications numerous sensing elements (greater than 10 or 20) across the sample are needed to provide high quality images and the rate with which the sensor is scanned across the surface needs to be fast enough to provide an image in real-time. With this parallel data acquisition architecture, wider areas can be scanned with the rapid generation of images.

To fully utilize the high data-rate measurement capability across numerous channels provided by this instrumentation requires the use of arrays of sensing elements. In particular, for imaging applications it is important for each sensing element to provide a response to the material under test, independent of the other sensing elements. One sensing array design for eddy current sensing applications on conducting and/or magnetic materials that minimizes this crosstalk between sensing element is the MWM™ geometry.

Figure 5:
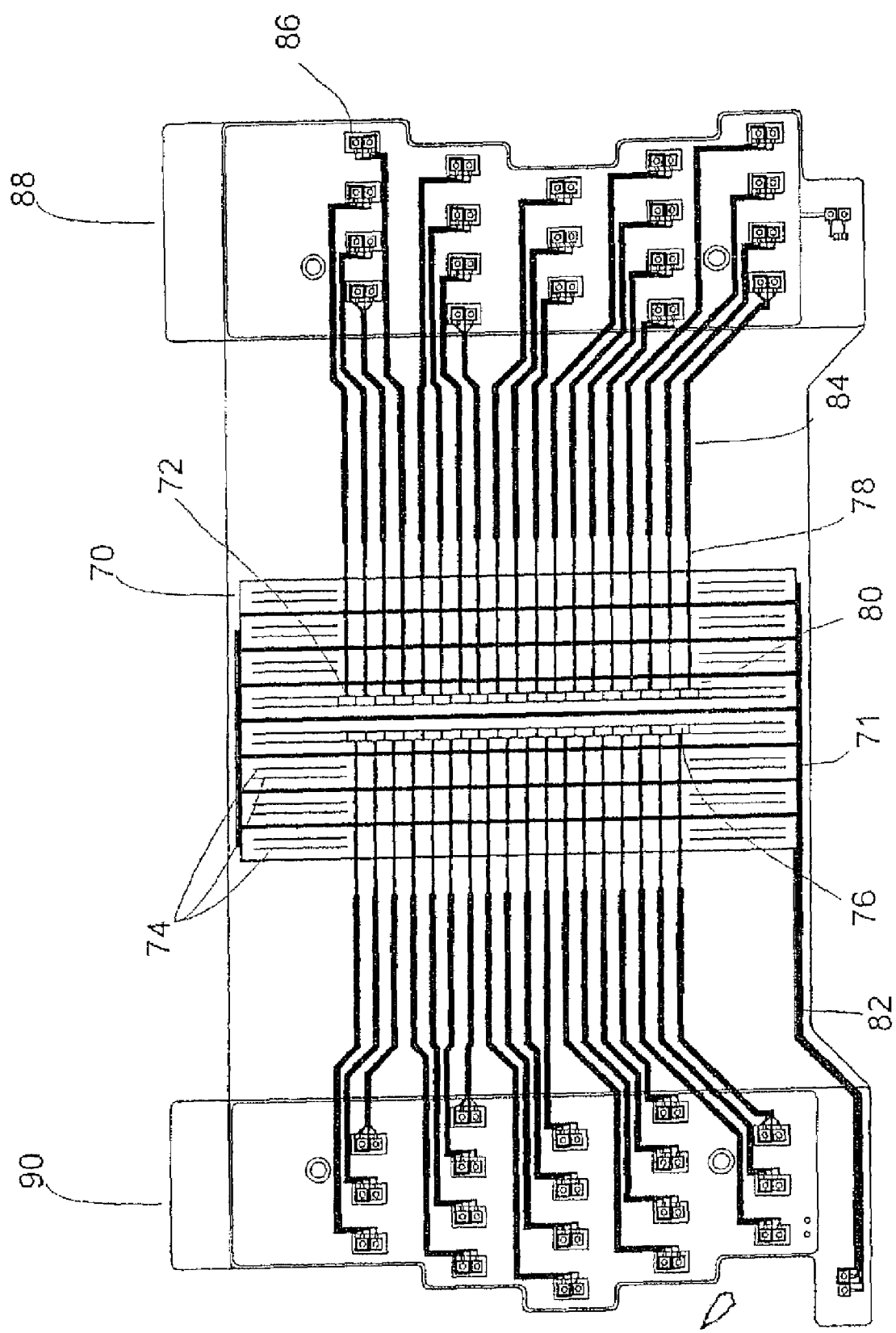
FIG. 5 is a drawing of a spatially periodic eddy current sensor array.

FIG. 5 illustrates an MWM-Array sensor, detailed descriptions of which are given in U.S. Pat. Nos. 5,015,951, 5,453,689, and 5,793,206, the contents of which are incorporated herein by reference in their entirety. The sensor includes a spatially periodic primary winding 70 having extended portions for creating the magnetic field and a plurality of secondary elements 72 within the primary winding for sensing the response to the material under test (MUT). Connecting segments 71 provide electrical continuity between the extended portions of the primary winding. The primary winding is fabricated in a periodic pattern with the dimension of the spatial periodicity termed the spatial wavelength $\lambda$. A current is applied to the primary winding and a voltage is measured at the terminals of the secondary elements. The secondary elements are pulled back from the connecting portions of the primary winding to minimize end effect coupling of the magnetic field. Dummy elements 74 can be placed between the meanders of the primary to maintain the symmetry of the magnetic field, as described in pending application Ser. No. 09/182,693, the contents of which are incorporated herein by reference in their entirety. The magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. No. 5,793,206, the contents of which are incorporated herein by reference in their entirety.

The MWM structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors. As indicated by Auld and Moulder, for conventional eddy-current sensors "nominally identical probes have been found to give signals that differ by as much as 35%, even though the probe inductances were identical to better than 2%" [Auld, 1999]. This lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the MUT, the sensor response can be accurately modeled which dramatically reduces calibration requirements. For example, in some situations an "air calibration" can be used where the response of the sensor in proximity to a test material referenced to the response of the sensor in air, distant from any conducting or magnetic materials. This calibration in air can be used to measure an absolute electrical conductivity without calibration standards, which makes the MWM sensor geometry well-suited to surface mounted or embedded applications where calibration requirements will be necessarily relaxed.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the conductivity and lift-off (where lift-off is defined as the proximity of the MUT to the plane of the MWM windings). For the characterization of coatings, cracks, or surface layer properties, three-dimensional versions of the measurement grids can be used for more than two unknowns, multiple frequencies, or multiple spatial wavelengths, or multiple lift-offs, or multiple states (such as temperature) or combinations of these can be used. Alternatively, the surface layer parameters can be determined from numerical algorithms that minimize the least squares error between the measurements and the predicted responses from the sensor.

An advantage of the measurement grid method is that it allows for real-time measurements of the absolute electrical properties of the material. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

In FIG. 5 the primary winding 70 is split into two parts, with every other loop of the primary winding connected together in series. Current through these two conducting loops imposes a spatially periodic magnetic field. This winding configuration minimizes the effects of stray magnetic fields from the lead connections to the primary winding, which can create an extraneous large inductive loop that influences the measurements, maintains the meandering winding pattern for the primary, and effectively doubles the current through the extended portions of the meanders.

To provide complete coverage when the sensor is scanned across a part or when a crack propagates across the sensor, perpendicular to the extended portions of the primary winding, secondary elements 76 in a primary winding loop adjacent to the first array of sense elements 72 are offset along the length of the primary loop. Additional primary winding meander loops, which only contain dummy elements, are placed at the edges of the sensor to help maintain the periodicity of the magnetic field. The connection leads 76 to the secondary elements are perpendicular to the extended portions of the primary winding, which necessitates the use of a multi-layer structure in fabricating the sensor. The layers that contain the primary and secondary winding conductors are separated by a layer of insulation. Layers of insulation are generally also applied to the top and bottom surfaces of the sensor to electrically insulate the primary and secondary windings from the MUT.

These leads to the primary and secondary elements are kept close together to minimize fringing field coupling. The leads for the primary winding 82 are kept close together to minimize the creation of fringing fields. The leads for the secondary elements 84 are kept close together to minimize the linkage of stray magnetic flux. The bond pads 86 provide the capability for connecting the sensor to a mounting fixture. The trace widths for the primary winding can also be increased to minimize ohmic heating, particularly for large penetration depths that require low frequency and high current amplitude excitations.

The size of the sensing elements can be adjusted to improve sensitivity to the flaw or property that needs to be detected. For example, to minimize coupling of short spatial wavelength magnetic field modes, the distance 80 between the sensing elements and the primary (drive) winding is made relatively large. As a result, the sensing element response is primarily sensitive to the dominant periodic mode. This produces improved depth of sensitivity to the properties of an MUT. The length of the secondary elements should be as small as possible to create a high resolution image when scanned over the surface of a part but also large enough so that a reasonable number of channels are used when scanning wide areas and the signal-to-noise is large enough to obtain reliable data. In one embodiment, an array of 19 one-eighth inch long elements was suitable for scanning over a more than two-inch wide area inspecting for subsurface inclusions tens of mils in size.

Figure 6:
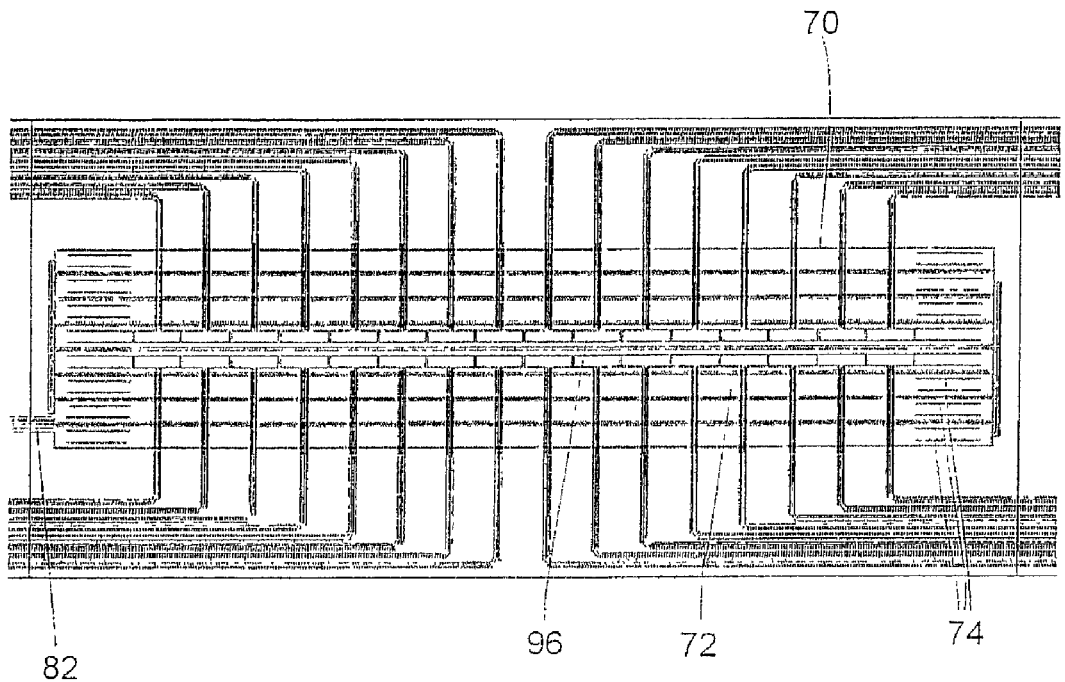
FIG. 6 is an expanded view of the drive and sense elements of a spatially periodic eddy current sensor array.
Figure 7:
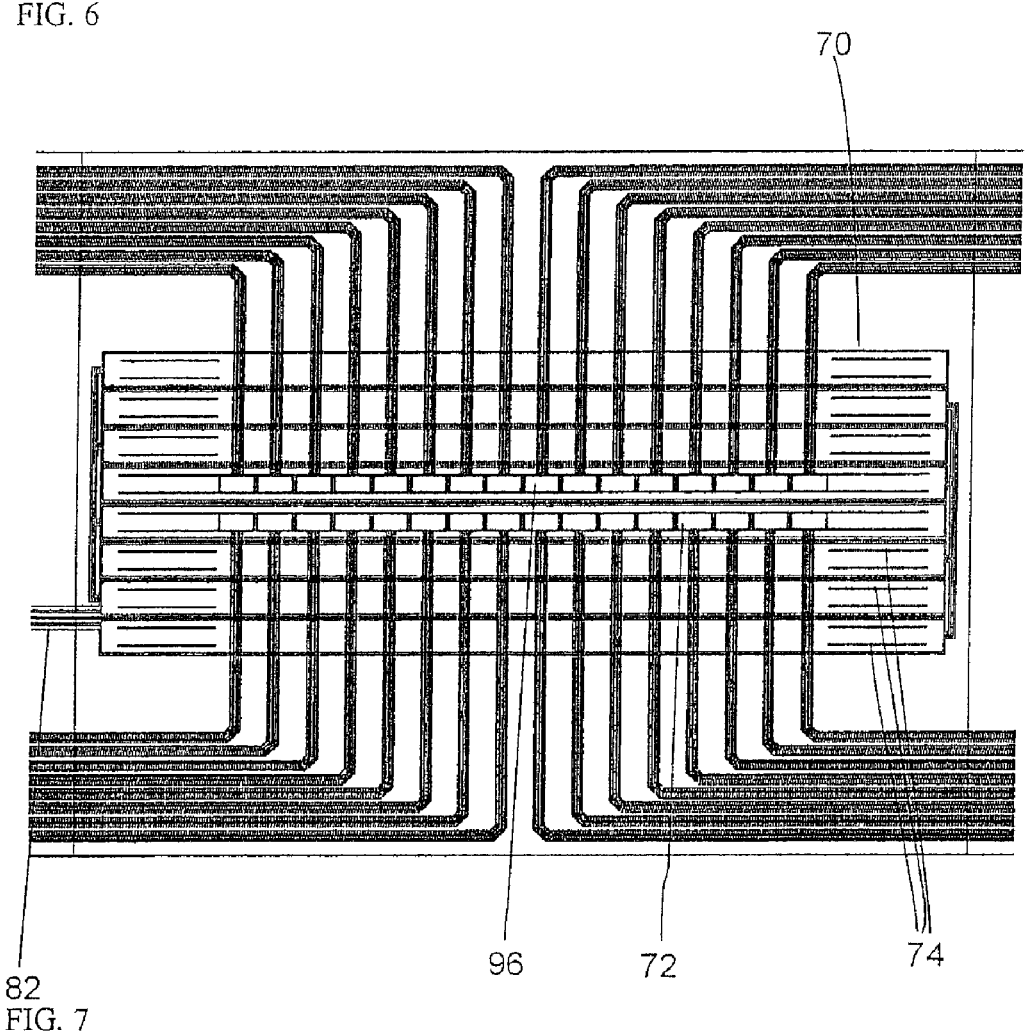
FIG. 7 is another expanded view of the drive and sense elements of a spatially periodic eddy current sensor array with smaller aspect ratio elements than illustrate in FIG. 6.

Two additional configurations for MWM-Arrays are shown in FIG. 6 and FIG. 7. In this case, the sensing elements 72 and 96 in adjacent loops of the primary winding are aligned with each other. Each channel provides redundant information or measurement data for the MUT when scanned in a direction perpendicular to the extended portions of the primary winding. Alternatively, the differential response between aligned sensing elements can be taken to enhance sensitivity to small defects. The sensing elements in FIG. 6 have a higher aspect ratio than the sensing elements in FIG. 7 so that the length of each sensing element is relatively long compared to the width of each element. In another embodiment, the redundant elements each respond to a flaw or anomaly at about the same time as it crosses the center linear drive segment (or segments). The signals from the redundant elements are then combined to improve sensitivity and reject false detections. In another embodiment, multiple frequencies are used with redundant elements to further improve sensitivity and reduce false alarms for shallow cracks.

Figure 8:
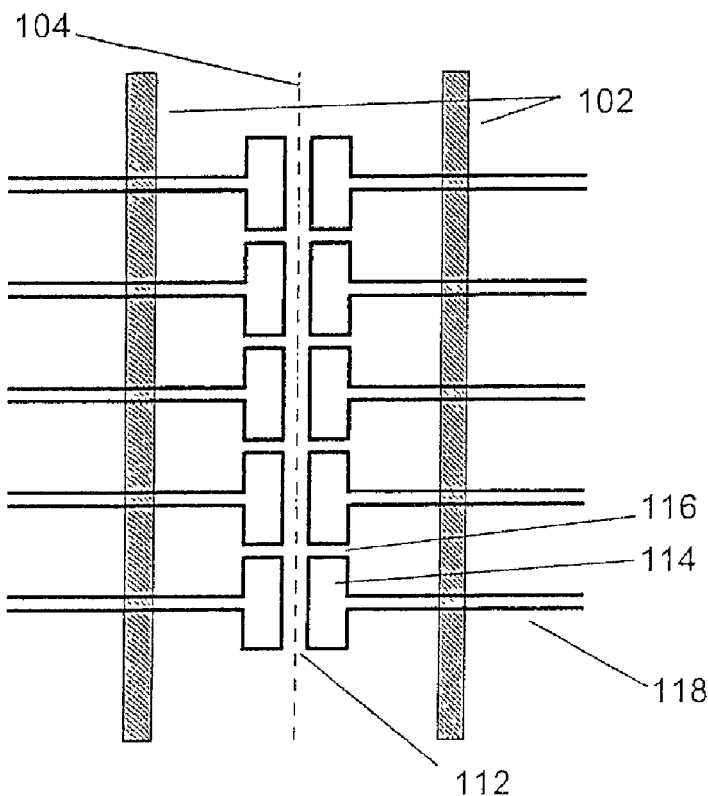
FIG. 8 shows alternative placement of sense elements for measuring a differential response.
Figure 9:
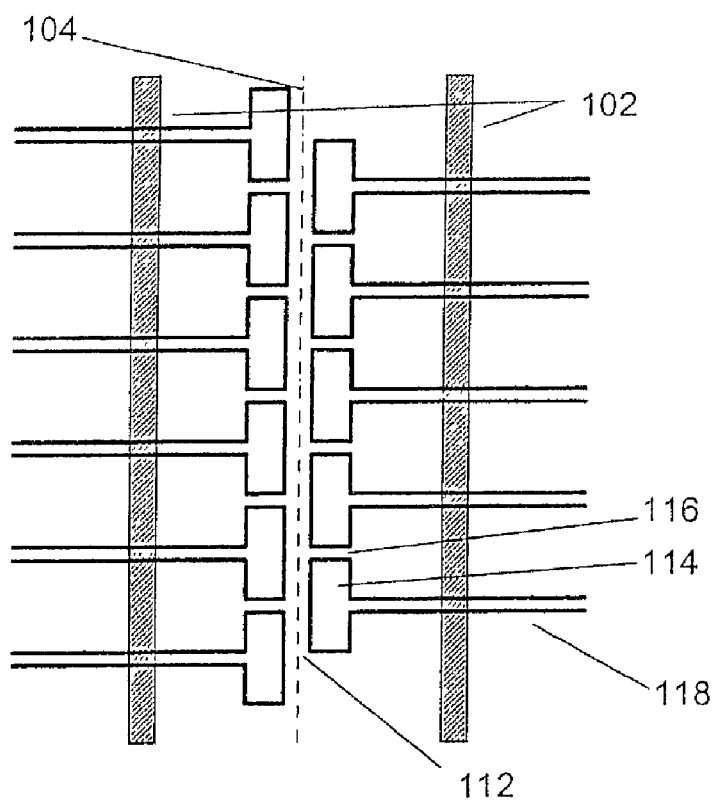
FIG. 9 shows alternative placement of sense elements for complete coverage when scanned over a material.
Figure 10:
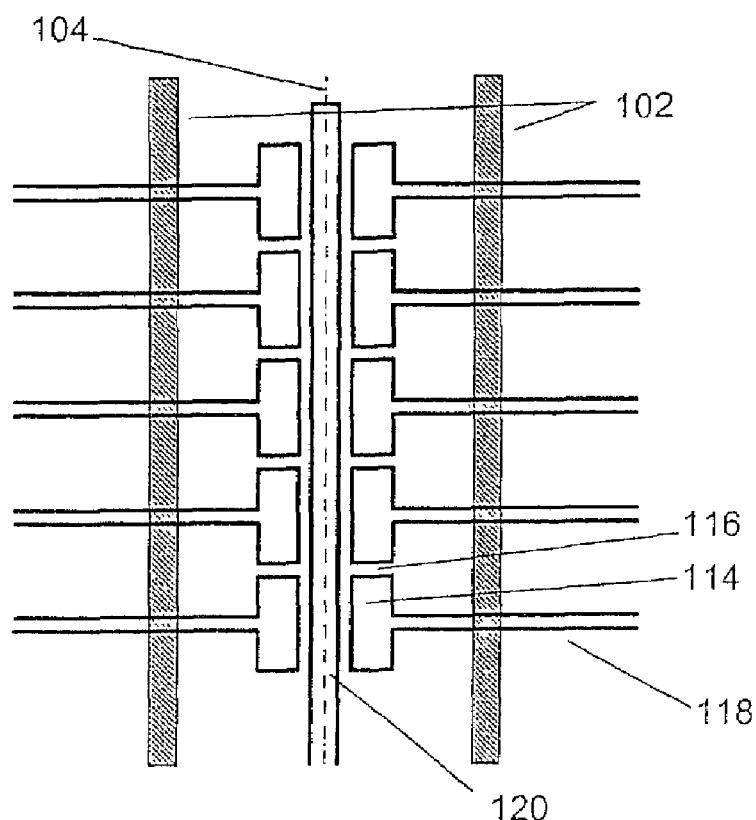
FIG. 10 shows a combination of small sense elements for imaging and a large sense element for absolute property measurements.

FIG. 8 shows an embodiment of the MWM-Array in which all of the sensing elements 114 are located between a single set of extended portions for the primary winding 102. The extended portions of the primary are connected at the ends in a fashion similar to connections 71 shown in FIG. 5. The sensing elements 114 are placed equal distances from the center line 104 between the extended portions of the primary and are aligned with each other along the length of the primary winding. For coupling to the deeper penetrating spatial modes the gap 112 should be minimized. Furthermore, to maximize coverage of the MUT when scanned in a direction perpendicular to the extended portions of the primary winding, the gap 116 should also be minimal. Alternatively, the sensing elements can also be staggered as shown in FIG. 9 to provide complete coverage of the MUT. In another embodiment, as shown in FIG. 10, a larger sensing element 120 or another drive element can also be placed directly between the two arrays of smaller sensing elements, at the center of the other primary winding segments. When this is a single element, this allows the differential response to be measured with the smaller sensing elements and the absolute response from the larger sensing element. This can facilitate compensation for lift-off variations across the part and the creation of images of the absolute properties of the MUT. The advantage of each of these designs is that all of the sensing elements are moved into a single portion of the primary, which allows the sensor size to be reduced. When the center element 120 is another drive element, the sensing elements close to the drive are more sensitive to small shallow flaws. Sensors with a central drive element are shown in FIGS. 6 and 7.

Figure 11:
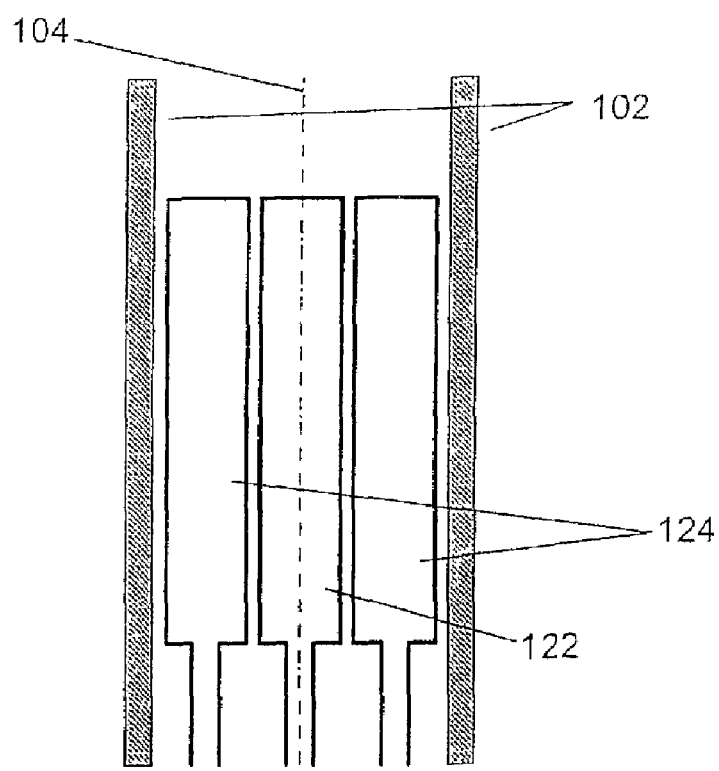
FIG. 11 shows a two wavelength sensor array having multiple sensing elements placed between a single pair of extended meanders for the primary winding.
Figure 12:
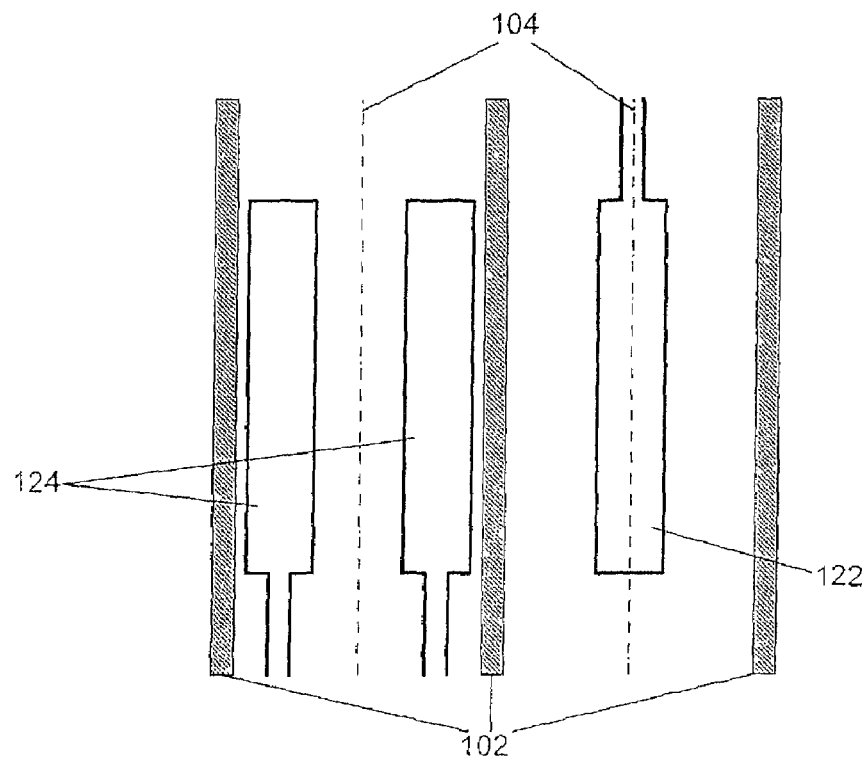
FIG. 12 shows a two wavelength sensor array having sensing elements placed at different distances from the primary winding meanders in separate pairs of extended meanders for the primary winding.

Multiple sensing elements can also be placed across the distance between the extended portions of a primary winding to provide sensitivity to different depths into a test material. FIG. 11 shows a set of three sensing elements placed between the extended portions of a primary winding 102. The extended portions of the primary are connected at the ends in a fashion similar to connections 71 shown in FIG. 5. The sensing element 122 located near the centerline 104 between the extended portions of the primary winding is sensitive to relatively deeply penetrating magnetic fields and to deep material properties. The sensing elements 124 located closer to the extended portions of the primary winding are sensitive to relatively shallow magnetic field penetration depths and to near surface material properties. The sensing element 122 responds to deeply penetrating or long wavelength spatial modes for the magnetic field while the sensing elements 124 respond to shallow penetration or short wavelength spatial modes for the magnetic field. Thus, the sensing element configuration is a two spatial wavelength sensor design and also provides the capability to simultaneously measure the response at multiple penetration depths. FIG. 12 shows an alternative design, which also provides multiple wavelength measurement capabilities. In the design of FIG. 12 the sensing elements are placed in different sets of extended portions between the primary windings. In addition, the connection leads to the sensing elements can be placed at either end of the sensing elements.

Figure 13:
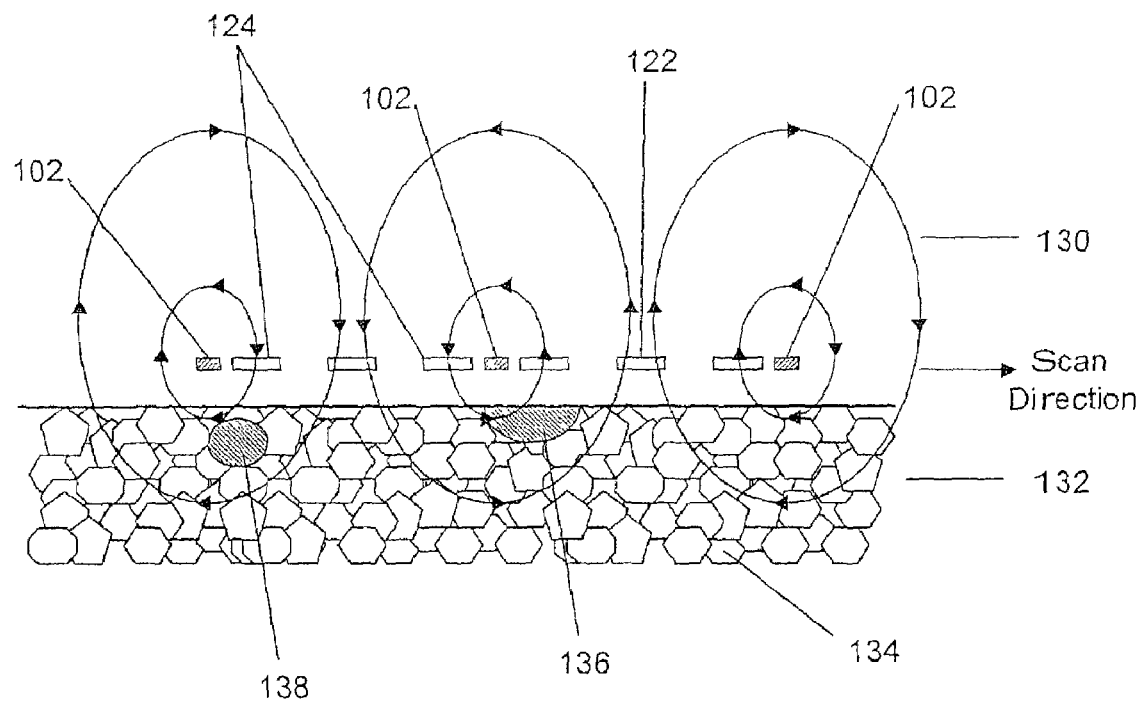
FIG. 13 shows a two wavelength sensor measurement over a test material having microstructural variations and anomalies.

The capability to measure multiple depths of penetration or spatial wavelengths simultaneously is particularly useful for the detection of flaws or anomalies in materials with significant microstructural variations. FIG. 13 illustrates one such measurement in which a periodic or non-periodic eddy current sensor is scanned over the surface of a test material 132 having relatively large grains 134. One such material is titanium. The microstructural variations from the grains affects the eddy currents induced in the material 132 and the magnetic field 130 that reaches the sensing elements 122 and 124. The results in measurement "noise" that prevents the detection of small defects in the test material either at the surface 136 or buried beneath the surface 138. The different paths for the magnetic field through the test material 132 can be used to suppress the effects of the microstructural noise and to enhance the detection capability for discrete anomalies such as cracks and inclusions.

These segmented field eddy current arrays that contain multiple sensing elements within the footprint of a single primary operate in three modes. In the first mode, the array of sensing elements is a single linear array at a fixed distance from the drive winding as in either row of FIG. 5. In this case the field of the drive is segmented for the purposes of increasing the sensor imaging resolution and the sensitivity to smaller defects. In the second mode, there are two or more linear arrays of sensing elements at different distances from the drive winding. In this case the field segmentation with varying distance from the primary. The goal here is to permit different sensing elements to sense magnetic flux that has passed through different paths in the material under test. In this case, as with phased array ultrasonics, an anomaly is seen by multiple sensing elements through different paths with different microstructure variations. The result is an averaging out of background microstructure noise contributions and an amplification of the signal from the anomaly after averaging and filtering the data from the sensing elements at different distances from the drive. This is valuable both for subsurface anomalies and surface breaking flaws. In the third mode, two different linear arrays are located at the same distance on each side of the drive as in FIG. 6 and FIG. 7. In this case, by using two elements on opposite sides of the drive, a flaw that is passing under the drive is simultaneously sampled by both sensing elements (this is also true for elements at different distances from the drive); thus, when these two sensing element responses are added (after lift-off compensation and filtering) then as above the path through the microstructure is different, averaging out noise, but the anomaly response is the same. Using multiple elements on each side of the drive and averaging the pairs at the same distance from the drive then scaling the data from each pair before averaging the pairs together provides a further method for enhancing the signal from an anomaly and suppressing the noise from a crack or other anomaly. Other filters can also be constructed by combining the responses at multiple sensing elements and also at multiple excitation frequencies.

The use of high resolution absolute conductivity mapping arrays, such as the MWM-Array, introduce the new capability to measure absolute electrical conductivity or to estimate the size and depth of an anomaly in a metal, or to estimate the size and depth of a surface breaking crack. To accomplish this the calibration and measurement procedures must be self-consistent, and the resulting measurements must be robust and reproducible to justify implementation in production or field inspection applications.

Conventional eddy current "pencil probes" used for inspection of engine components, for example, are often calibrated using crack standards. For example, the signal from a typical crack might be recorded and then the range on the instrument might be set so that the crack response is at 80% of the total scale. Then, a threshold might be set so that some minimum crack size is detectable on the standard. This is a useful method if the crack standard well represents the actual component that is being inspected for cracks. Unfortunately, standards that are flat and contain simulated flaws (e.g., fatigue cracks grown from EDM notches with the notches later broached and then the surface etched to "reveal" the cracks) are generally used to determine the POD (probability of detection) for a given flaw size. This is a useful method only when the component is well represented by the standard. If for example, the probe scanning the actual component is at a higher lift-off (e.g., proximity of the sensor to the surface is not as close) than it was on the standard when the thresholds were set, then the actual detectable crack size would be larger (and perhaps much larger) than assumed.

One advantage of using an absolute sensor, such as the MWM-Array with grid methods is that the lift-off can be measured at each data point during a scan and at each individual sensing element. Thus, in one preferred embodiment the MWM-Array is first scanned across a reference crack standard at several different lift-offs, and the crack detection threshold on the effective electrical conductivity measured by the MWM at each sensing element is determined at each lift-off. Then depending on the lift-off the detection threshold is now automatically adjusted to the appropriate level. The true probability of detection may then be known for the lift-off in a production or field inspection. This is not possible with a lift-off compensated differential eddy current probe that does not accurately measure the lift-off independently.

The method described above still relies on crack standards. In a second preferred embodiment the detection of cracks and the calibration procedure is performed without calibrating on the crack standards. First, the sensor is calibrated in air or on a reference part (with and without a lift-off shim to vary the lift-off by a known amount). Then the sensor is scanned across the actual part surface to determine the background "noise" level. Then the crack (or other anomaly) detection threshold is set based on the signal to noise level for discrete anomalies in the case of discrete cracks. In one preferred embodiment the sensor can be scanned in an orientation that is insensitive to cracks first and then in the orientation that is sensitive to cracks. Any crack-like signals are then removed to establish the noise level and set the signal to noise based crack detection threshold. This method is important for detection of cracks on relatively rough surfaces such as in fretting regions or shot peened surfaces.

Figure 14:
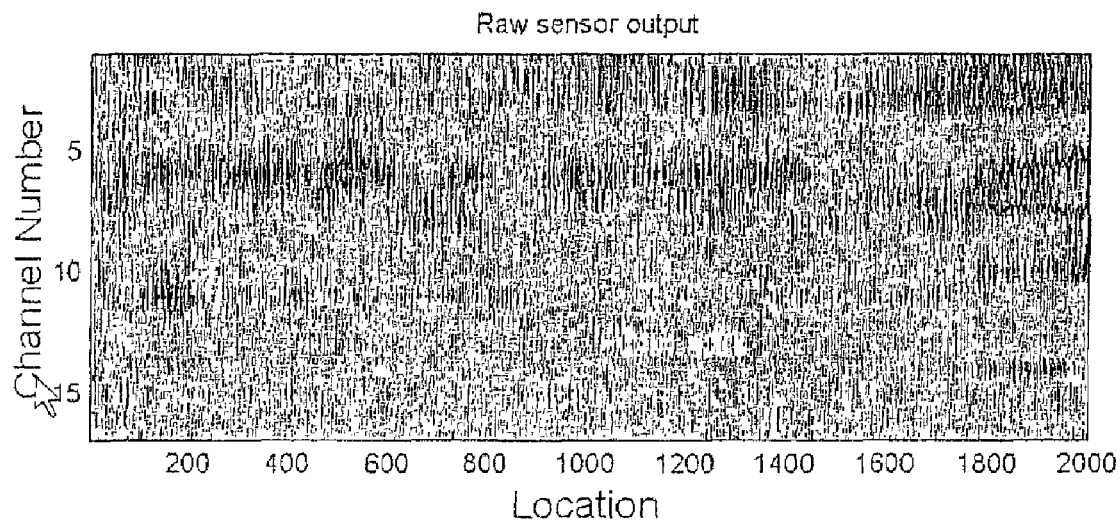
FIG. 14 shows a measurement image of the raw data for a metal plate containing several inclusions.
Figure 15:
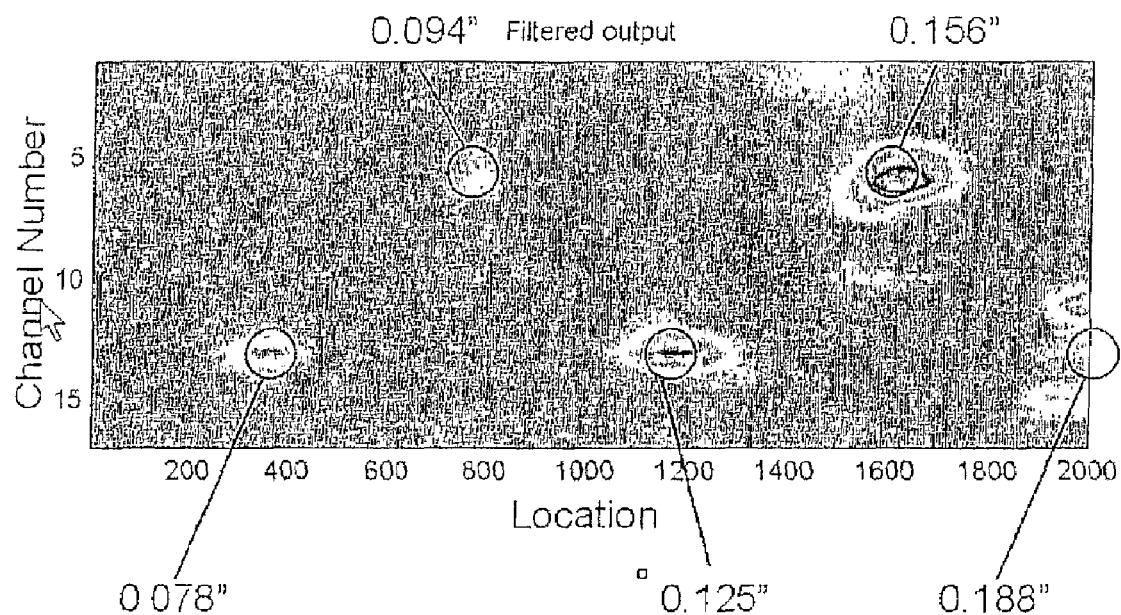
FIG. 15 shows the measurement image of FIG. 14 after processing with a shape matching filter.
Figure 16:
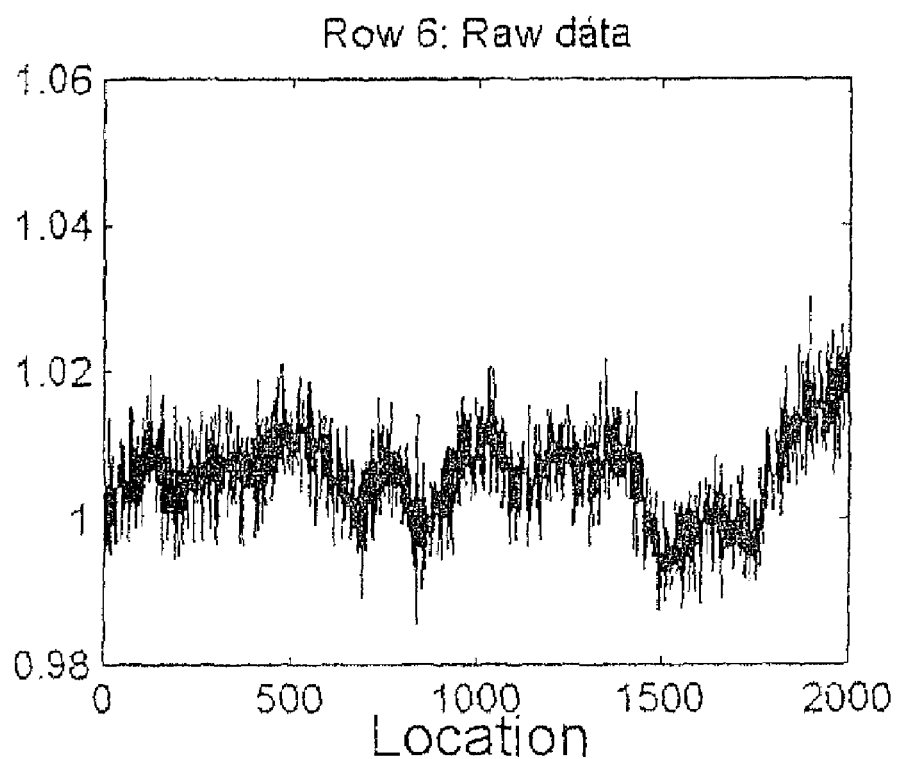
FIG. 16 shows the data from row 6 for the measurement of FIG. 14 prior to shape match filtering.
Figure 17:
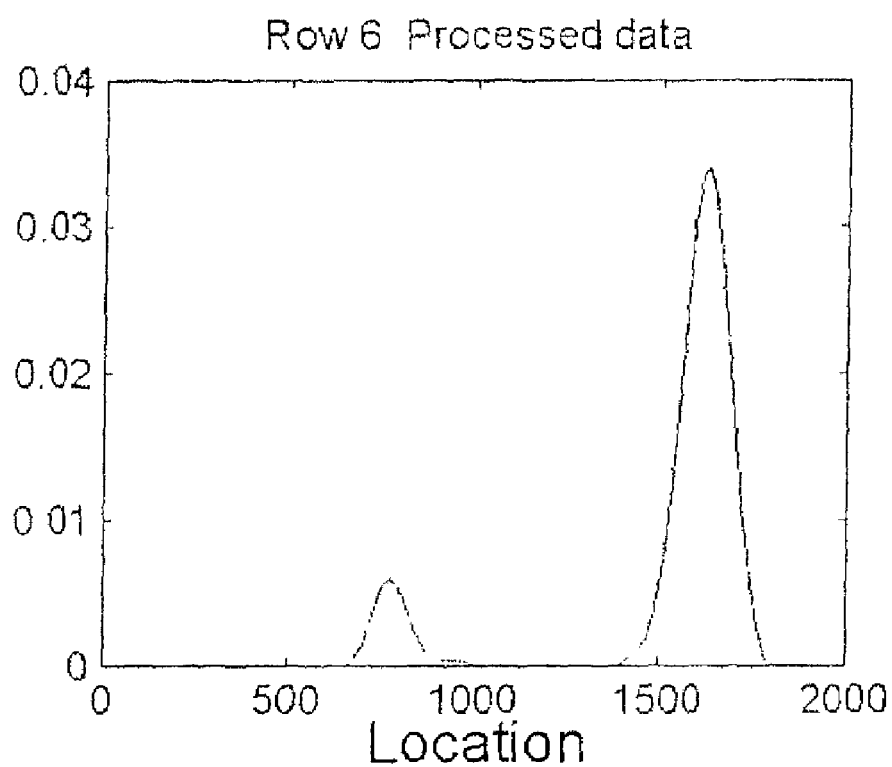
FIG. 17 shows the data from FIG. 16 after shape match filtering.
Figure 18:
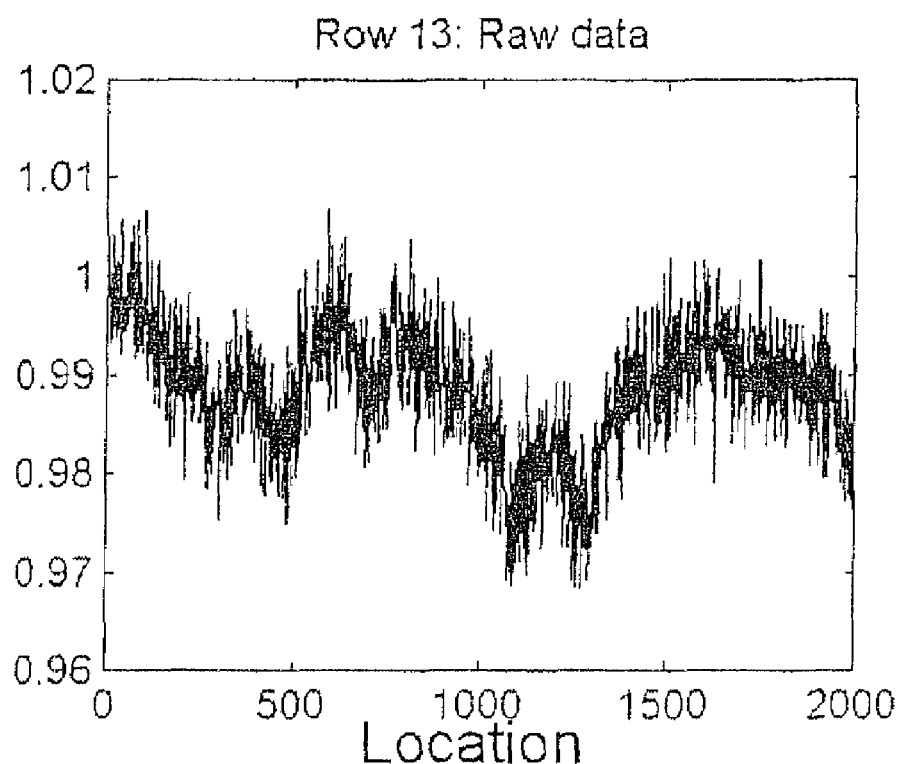
FIG. 18 shows the data from row 13 for the measurement of FIG. 14 prior to shape match filtering.
Figure 19:
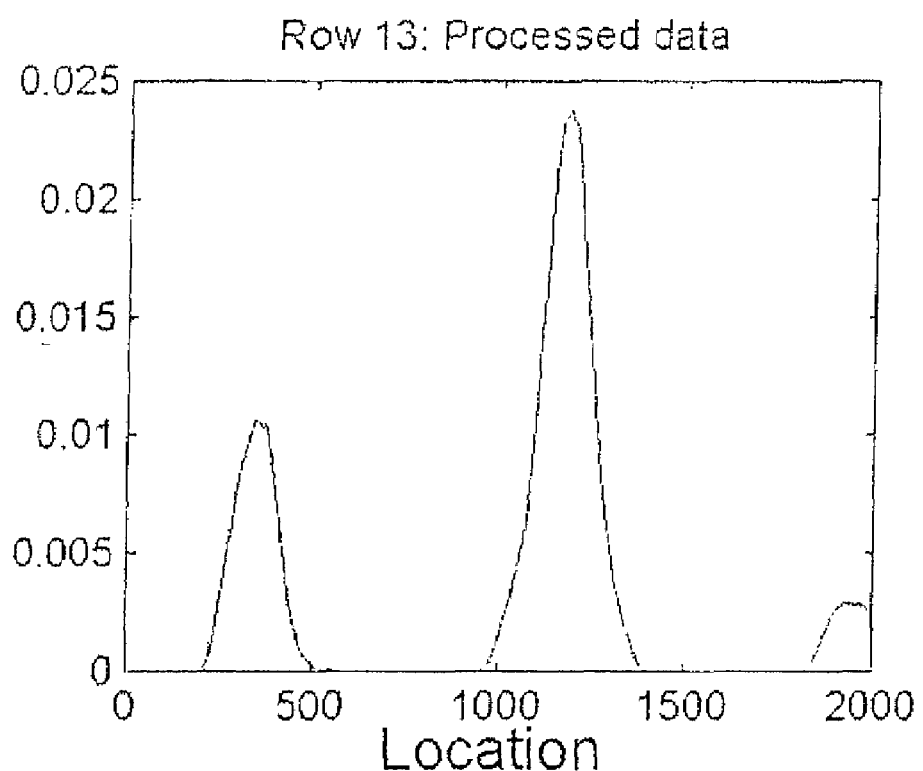
FIG. 19 shows the data from FIG. 18 after shape match filtering.

Along with the capability to measure images of the material properties, processing of these images can play a critical role in providing a meaningful inspection technique. For the detection of flaws or fatigue damage, matched filters can be used to extract the characteristic signal from a feature from a noisy signal. As an example, consider the images illustrated in FIG. 14 for a scan over a metal plate having artificial inclusions of various sizes hidden more than 0.075 inches beneath the surface. FIG. 14 shows the raw normalized conductivity measurement scan while FIG. 15 shows a conductivity scan over several of the inclusions processed with a shape matching filter. The raw conductivity scan image is relatively noisy so that the positions of the inclusions are not readily evident. Processing with the shape filter extracts the portions of the signals in each row that have a shape similar to the double peak signature associated with scanning a spatially periodic sensor, such as the MWM, over a feature in the MUT. The resulting image of the processed conductivity tends to show the inclusions along with some other features of the sample that are similar to inclusions. Plots of the raw conductivities for the sensor element rows that passed directly over the inclusions are shown in FIG. 16 for row 6 and FIG. 18 for row 13. The corresponding processed conductivities are shown in FIG. 17 for row 6 and FIG. 19 for row 13. The presences of the defects are clearly identified after processing with the shape matching filter. In each of these plots the horizontal axis or location is given by an index value and spans approximately 4 inches. In another embodiment, the response from redundant elements on opposite sides of a linear drive can be added or combined. If added, a three humped response is then produced and matched filters with three humps are used to process data. In another embodiment, the spacing between the drive and sense elements and/or the sensing element size is selected to achieve high sensitivity to anomalies or properties of interest.

Although a simple match filter works well for features of a specific size, the match becomes poor and results in artifacts in the response if a feature is detected that is substantially larger or smaller than the feature used to create the match filter. To improve the performance, multiple passes can be used with matched filters of a specific feature size, or adaptive filters can be applied to the data. As an example of an adaptive filter, for well-separated indications after scanning across the plate and filtering with the match filter, one can take a window around the spot on the plate where a strong match was detected and fit a two humped Gaussian distribution to the data. There are four parameters per hump in the distribution, describing the amplitude, location, and shape, which results in eight parameters that can describe the properties of each indication. These results can then be used to determine the symmetry of the response and possibly the size and depth of the feature. In addition, filtering can also be applied across each of the element rows at a given location, as is done in conventional image processing.

Figure 20:
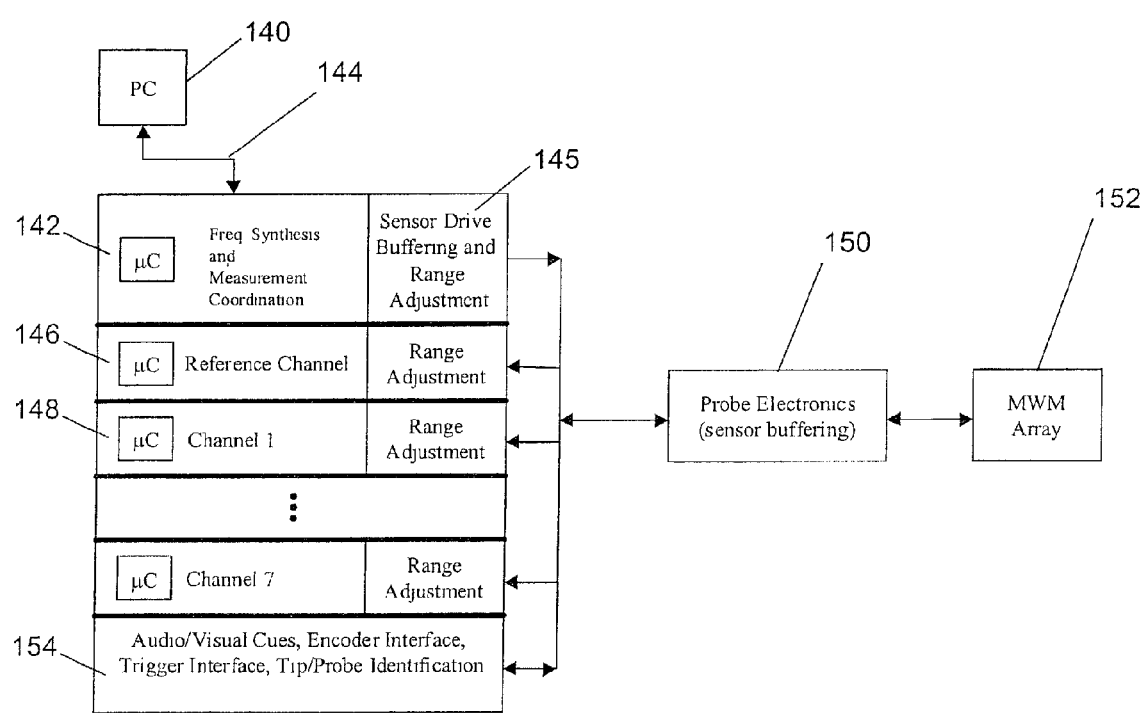
FIG. 20 is a simplified schematic for an impedance instrument.

FIG. 20 shows another schematic for an impedance instrument that includes a microcontroller. This simplified schematic shows a serial RS-422 communication line 144 between the computer 140 and the master microcontroller 142. This master controller is used to synthesize the drive signal, which is then amplified by a buffer 145 before passing to the probe electronics 150 and the sensor array 152. In this instrument, the drive signal is measured on a reference channel 146 and the sensor responses are measured on up to seven other channels 148. The master controller provides coordination between the measurement channels. In this embodiment, additional instrument capabilities 154 are also provided. These capabilities include audio or visual cues such as buzzers or displays for the operator user interface, an interface for input from a position encoder for monitoring the spatial location of the sensor array, a trigger interface for data acquisition control, and measurement circuitry that can be used for identification of the sensor tip or probe being used.

Figure 21:
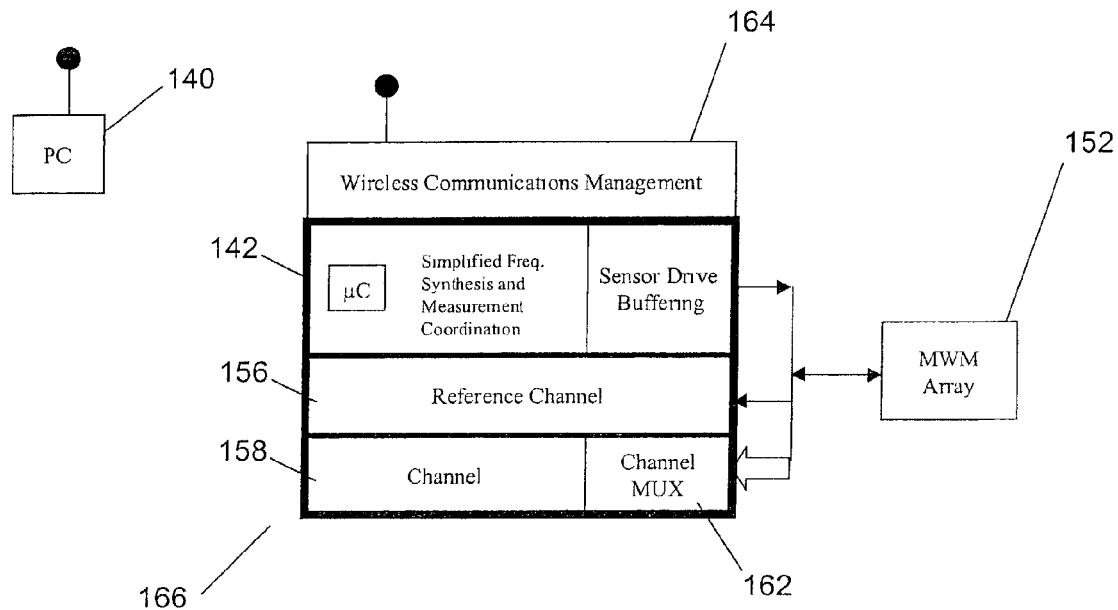
FIG. 21 is a simplified schematic for an impedance instrument that includes a wireless connection.

In some measurement applications, such as the monitoring of permanently mounted sensors distributed across an aircraft structure, the sensors and sensor array must be located at a distance from the host computer. For these remote inspection applications, it is not always practical to run individual communication lines between the computer and the impedance measuring instrumentation or the sensor arrays. Instead, it is more practical to use communication lines and protocols that permit multiple transmit and receive devices to be connected to the same line, such as RS-485 or wireless communication techniques based, for example on 8.0211b or Bluetooth™ standards. FIG. 21 shows a simplified architecture for an impedance instrument that incorporates a wireless communication technique 164. In this case the impedance measurement block 166 has independent power control, a reference channel 156 is used to measure the drive single, a single measurement channel 158 is used to monitor the response of the elements in the sensor array 152. A multiplexer 162 is used to select the current channel being measured. In this particular configuration, the reference and channel data acquisition circuitry still include filters and mixers but a microcontroller is not used for each data acquisition circuit.

A wireless or remotely distributed instrument architecture has different design constraints than a local parallel channel instrumentation architecture. For example, a wireless instrument that incorporates an independent power source, such as a battery, should shut down components when not they are not in use between measurements. A local wired system with access to a power source does not necessarily need these power saving features and may have additional functionality for the monitoring of embedded sensors, such as audio/visual cues, encoder support, automatic probe and sensor tip identification, and multiple trigger sources.

For making the wireless device as small and compact as possible there are also tradeoffs that can be made in terms of the excitation frequency range for the instrument. For example, a desktop instrument may have a relatively broad excitation frequency range of 6 kHz to 32 MHz. For the lower excitation frequencies, more power is generally used to drive larger currents in the sensor in order to achieve reasonable measurement sensitivity with an eddy current sensor. Consequently, raising the lower limit for the excitation frequency up to, for example 100 kHz, reduces the measurement capabilities of the instrument but has a lower power requirement and provides a longer battery life-time. In addition, a higher excitation frequency also reduces the complexity of the filter used to isolate the dc component of the signal obtained after mixing the measurement signal with the reference signal. Sharp filters, such as fifth order filters, are needed when the excitation frequency is near the filter cutoff frequency; when the excitation frequency is relatively high compared to the filter cutoff frequency, simpler filters, such as first order filters, can be used. Longer integration times could also be used to perform measurements at the lower frequencies, but there would still be constraints on the power that could be consumed. On the high frequency end of the range, a simpler frequency synthesizer can be used if lower excitation frequencies are used. This also permits longer lead lengths between the sensor and the local electronics for performing the measurements. An example limited frequency range for a wireless instrument is 100 kHz to 10 MHz. In an even simpler embodiment, a single measurement frequency would be used.

Other design constraints for a wireless instrument involve the data acquisition speed, the number of channels available for processing, and the ranging capabilities of for the sensing signal. One basic tradeoff is between higher data acquisition rates and the additional size, weight, power consumption, and circuit complexity of the instrument. For example, a desktop instrument may have a sharp fifth order filter and a separate measurement channel for each sensing signal input with acquisition of the data in parallel. This permits relatively rapid data acquisition rates, such as 6 msec for acquisition from all channels. In contrast, a simplified instrument for wireless operation may use a simple first order filter so that the data acquisition time is 50 msec per channel. This device may also use a multiplexer so that a single measurement channel can be used and cycled through each sensing input. In one embodiment, separate measurement channels are used for the reference signal and the sensing input signal. This allows parallel measurements of the reference with each sensing input signal, and accurate compensates for any drift in the reference or drive signal. In this configuration, the data acquisition time then simply increases with the number of sensing inputs being multiplexed together. For example, for a seven sensing input device, the data acquisition time is seven times longer than for a single sensing input device. In another embodiment, the same measurement channel is used for the reference signal and the sensing input signal so that the reference signal is also multiplexed into the measurement channel. For a single sensing input, the data acquisition time is twice as long as the time required when the reference is measured in parallel with the sensing input. The reference signal can be measured prior to (or after) all of the measurements of the sensing inputs if the drive signal is stable and does not drift. However, a more stable measurement is obtained when the reference signal is measured immediately prior to (or after) each sensing input measurement at the expense of slower data acquisition. A desktop instrument may also including automatic ranging features that allow the current amplification or gain settings to be set dynamically. For a wireless device, these range levels or gain settings should be fixed at a constant value.

Several levels of multiplexing can be performed. In the simplest configuration, a single multiplexer is connected to a single multiple element sensor array, multiple single element sensors, or a combination of the two. Preferably, the drive signal to each sensor primary winding would be multiplexed, along with sensor element signals, to conserve power. Large multiplexers can be used to connect several multiple element sensor arrays to a single instrument, such as two or more seven-channel sensors, however this also causes an increase in the power requirement as each channel of the multiplexer generally has a quiescent power requirement. Preferably, the disable mode of multiplexer operational amplifiers is use to limit any quiescent current requirements and the components are shut down until needed.

Depending upon the measurement application, the resolution of the impedance measurement may also be limited for a wireless instrument. The wireless instrument can be designed to have the equivalent resolution of a desktop instrument, such as complex (real and imaginary parts) of the impedance with 16 bits for each part. However, if permitted in the application, a more simple impedance magnitude measurement with a 12 or 16 bit representation may be performed. The resolution of the impedance information also affects the requirements for any buffering of the data. In one configuration, no buffering is performed in the wireless device and data is uploaded as necessary. In another configuration, the data is stored in static memory at predetermined intervals or when triggered.

Figure 22:
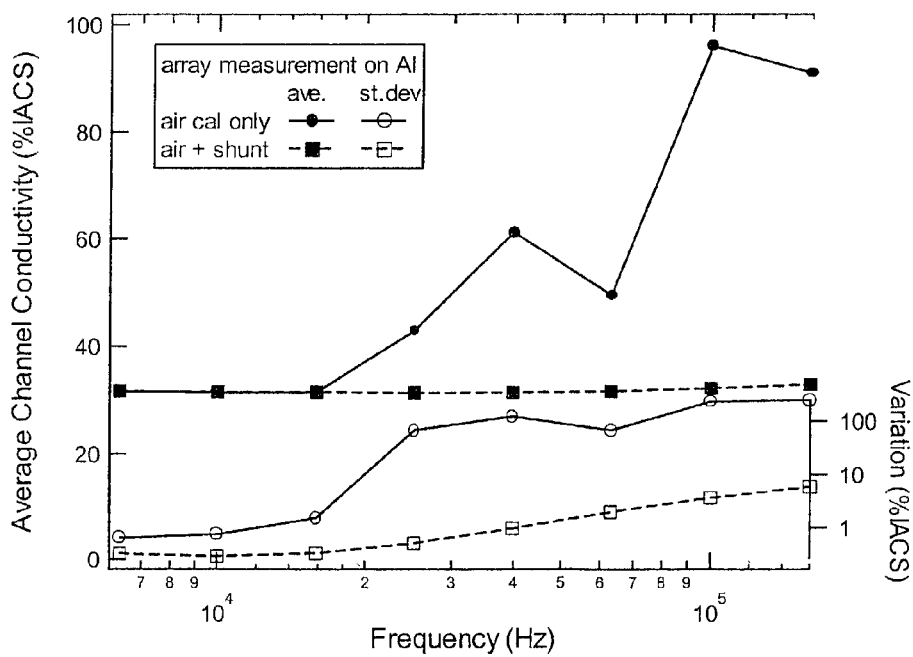
FIG. 22 is a plot of the average and standard deviation electrical conductivity for an array of sensing elements using an air calibration and an air plus shunt calibration.

The method of calibration of the sensing arrays also has an impact on the quality of the measurement image obtained. FIG. 22 shows a plot of the average conductivity for an MWM-Array containing 37 sensing elements or channels at several frequencies ranging from 6 kHz to 158 kHz. As described in U.S. Pat. No. 6,188,218, the contents of which are incorporated herein in their entirety, the response of the sensor in air can be used to set calibration coefficients for each sensing element so that absolute property measurements can then be obtained from each sensing element when the array is placed in proximity to a test material. However, slight variations in the response from element to element can lead to striping and artifacts in material property images when the array is scanned over a test material. Often, the variation of a few channels, even as low as one to three, can have a significant impact on the average conductivity and can seriously degrade the quality of the image.

One method for reducing this variability in the response between elements is to perform a reference calibration on a defect-free portion of the test material or a material having a known conductivity. The disadvantages of this approach include that it requires knowledge of the reference material conductivity and properties, such as a uniform conductivity with depth and this approach is sensitive to ambient temperature variations since the conductivity or most materials varies with temperature. An alternative method for reducing the element-to-element variability is to calibrate in air and to also use measurements of the response of a shunt array to determine parasitic responses (e.g., capacitances and inductances). A comparison of the average conductivity across all of elements at several frequencies, using both an air calibration alone and an air plus shunt calibration, are shown in FIG. 22. The air plus shunt calibration yields an essentially constant average conductivity across the frequency range. The element-to-element variations, indicated by a plot of the standard deviation of the electrical conductivity estimates across the channels, is also substantially reduced, particularly at the higher frequencies.

The inventions described here relate to methods and apparatus for the nondestructive measurements of materials using sensors that apply electromagnetic fields to a test material and detect changes in the electromagnetic fields due to the proximity and properties of the test material. Although the discussion focused on magnetoquasistatic sensors, many of the concepts extend directly to electroquasistatic sensors as well.

While the inventions has been particularly shown and described with reference to preferred embodiments thereof, it will be understood to those skilled in the art that various changes in form and details may be made therein without departing from the spirit and scope of the invention as defined by the appended claims.

Reference Incorporated by Reference in its Entirety:

Auld, B. A. and Moulder, J. C. (1999), "Review of Advances in Quantitative Eddy-Current Nondestructive Evaluation," Journal of Nondestructive Evaluation, vol. 18, No. 1.

What is claimed is:

1. An apparatus for measuring electrical impedance for multiple elements of a sensor array comprising:
a signal generator controlled by a master microcontroller that creates a sinusoidally time varying excitation signal with at least one prescribed frequency which is applied to a conducting drive of the sensor array;
a plurality of data acquisition channels, each data acquisition channel measuring a signal from an individual sense element, and each data acquisition channel including a data acquisition microcontroller and an analog to digital converter, the measuring of the signal being triggered by the master microcontroller of the signal generator, with an in-phase response measured for each channel simultaneously at each prescribed frequency, and a quadrature phase response measured for each channel simultaneously at each prescribed frequency;
a computer for processing and storing measured values;
a plurality of data communication lines connecting the sensor array and the plurality of data acquisition channels; and
separate communication lines between the computer and the signal generator master microcontroller and between the computer and each data acquisition microcontroller.

2. The apparatus as claimed in claim 1 wherein each data acquisition channel measures the channel impedance in parallel with other data acquisition channels.

3. The apparatus as claimed in claim 1 wherein the signal generator master microcontroller and a first data acquisition microcontroller share a communication line.

4. The apparatus as claimed in claim 1 further comprising at least one probe element and electronic circuitry for processing each probe signal.

5. The apparatus as claimed in claim 4 wherein the probe elements are magnetic field eddy current sensing elements.

6. The apparatus as claimed in claim 5 where the circuitry to measure the electrical current to eddy current drive winding is located adjacent to the probe elements.

7. The apparatus as claimed in claim 4 wherein the probe elements are electric field capacitive sensing elements.

8. The apparatus as claimed in claim 7 where the circuitry to measure the electrical signal for the drive electrode is located adjacent to the probe elements.

9. The apparatus as claimed in claim 1 wherein the computer is remote and distant from the microcontrollers.

10. The apparatus as claimed in claim 1 further comprising:
a multiplexer between the sensor array and a data acquisition channel.

11. An apparatus for measuring electrical impedance for multiple elements of a sensor array comprising:
a signal generator controlled by a master microcontroller that creates a sinusoidally time varying excitation signal with at least one prescribed frequency which is applied to a conducting drive of the sensor array, the sensor array having a plurality of sense elements calibrated to have identical responses at the prescribed frequency for identical properties of a test material located proximate to each sense element;

a plurality of data acquisition channels, each containing a data acquisition channel microcontroller, an amplifier having the same gain for each channel, and analog to digital converter to measure a signal from an individual sensing element, the measurement being triggered by the master microcontroller, with an in-phase response measured for each channel simultaneously at each prescribed frequency, and a quadrature phase response measured for each channel simultaneously at each prescribed frequency;

a computer for processing and storing measured values;

a communication line between the computer and master microcontroller; and separate communication lines placed between the master controller and channel microcontrollers for handshaking.

12. The apparatus as claimed in claim 11 wherein the master microcontroller triggers the measuring of the signal and coordinates data acquisition and transmission to the computer.

13. The apparatus as claimed in claim 11 wherein each data acquisition microcontroller shares a communication line with the master microcontroller.

14. The apparatus as claimed in claim 11 wherein additional lines connect the data acquisition microcontrollers to the computer.

15. The apparatus as claimed in claim 11 wherein the computer is remote and distant from the microcontrollers.

16. The apparatus as claimed in claim 11 further comprising:

a multiplexer between the test circuit and the at least one data acquisition channel.

17. An apparatus for measuring electrical impedance for multiple elements of a sensor array comprising:

a signal generator controlled by a master microcontroller that creates a sinusoidally time-varying excitation signal with at least one prescribed frequency which is applied to a conducting drive of the sensor array;

a plurality of data acquisition channels, each containing a data acquisition microcontroller and analog to digital converter to measure a signal from an individual sensing element, the measuring of the signal being triggered by the master microcontroller, with an in-phase response measured for each channel simultaneously at each prescribed frequency, and a quadrature phase response measured for each channel simultaneously at each prescribed frequency; the plurality of data acquisition channels being separated into at least one group having a common communication line for data transmission within a group;

a computer for processing and storing measured values; and a communication line between the computer and master microcontroller.

18. The apparatus as claimed in claim 17 wherein a common communication line connects each group of data acquisition channels to the host computer.

19. The apparatus as claimed in claim 17 further comprising a plurality of probe elements and electronic circuitry for each probe signal.

20. The apparatus as claimed in claim 19 wherein the probe elements are magnetic field eddy current sensing elements.

21. The apparatus as claimed in claim 20 wherein the circuitry to measure the current to the eddy current drive winding is near the probe elements.

22. The apparatus as claimed in claim 19 wherein the probe elements are electric field capacitive sensing elements.

23. The apparatus as claimed in claim 22 wherein the circuitry to measure the voltage of the drive electrode is near the probe elements.

24. A method for measuring electrical impedance for multiple elements of a sensor array comprising:

passing a sinusoidally time-varying excitation signal having at least one prescribed frequency, amplitude, and phase set by a signal generator controlled by a master microcontroller into conducting drive of the sensor array;

simultaneously measuring a plurality of electrical signals from the sensor array using at least one data acquisition channel containing a microcontroller and analog to digital converter, with an in-phase response measured for each channel simultaneously at each prescribed frequency, and a quadrature phase response measured for each channel simultaneously at each prescribed frequency, the measuring of the signal being triggered by the master microcontroller wherein measuring the of each electrical signal of the plurality of electrical signals comprises:

mixing each electrical signal with a reference signal to produce a mixed signal, filtering the mixed signal with a low-pass filter to produce a result signal, converting the result signal into digital data, reading the digital data with the channel microcontroller to produce channel data; and transmitting the channel data to a computer for processing and storing measured values.

25. The method as claimed in claim 24 wherein the sensor array is an inductive sensor array.

26. The method as claimed in claim 24 wherein the sensor array is capacitive sensor array.

27. The method as claimed in claim 24 wherein the electrical signal from the sensor array is amplified and buffered.

28. The method as claimed in claim 24 wherein the reference signal has the same frequency as the excitation but a phase that can be switched between 0 degrees and 90 degrees when the cut-off frequency for low pass filter is less than one-half the excitation frequency.

29. The method as claimed in claim 24 wherein the reference signal description is set with a dc signal and correlated with the electrical signal when the cut-off frequency for low pass filter is greater than the excitation frequency.

30. The method as claimed in claim 24 wherein the master microcontroller coordinates analog to digital conversion, data transmission and frequency selection.

31. The method as claimed in claim 24 wherein the computer is remote and distant from the microcontrollers.

32. The method as claimed in claim 24 further comprising:

multiplexing some of the electrical signals from the sensor array before measuring them with the at least one data acquisition channel.

* * * * *